United States Patent [19]

Nishi et al.

[11] Patent Number: 5,559,224

[45] Date of Patent: Sep. 24, 1996

[54] CARBEPENEM DERIVATIVES

[75] Inventors: Toshiyuki Nishi; Hiroko Koda; Kazuyuki Sugita; Yohhei Ishida; Makoto Takemura; Takeshi Hayano, all of Tokyo, Japan

[73] Assignee: Daiichi Pharmaceutical Co., Ltd., Tokyo, Japan

[21] Appl. No.: 435,271

[22] Filed: May 5, 1995

Related U.S. Application Data

[63] Continuation of Ser. No. 167,965, filed as PCT/JP92/00790, Jun. 19, 1992, published as WO93/00344, Jan. 7, 1993, abandoned.

[30] Foreign Application Priority Data

Feb. 18, 1992 [JP] Japan ................................. 4-031054
Jun. 20, 1992 [JP] Japan ................................. 3-148469

[51] Int. Cl.⁶ ............................................. C07D 487/04

[52] U.S. Cl. .................................................... 540/350
[58] Field of Search ........................................ 540/350

[56] References Cited

U.S. PATENT DOCUMENTS 5,095,013  3/1992  Nakagawa et al. ...................... 540/350
5,122,604  6/1992  Sunagawa et al. ...................... 540/350

*Primary Examiner*—Rebecca Cook
*Attorney, Agent, or Firm*—Sughrue, Mion, Zinn, Macpeak & Seas

[57] ABSTRACT

Carbapenem derivatives which may be utilized as antibiotics and which show strong antibacterial activity against various bacterial strains including *Pseudomonas aeruginosa*. The compounds containing the derivatives are quite safe and are also stable against hydrolases such as dehyropeptidase (DHP).

6 Claims, No Drawings

CARBEPENEM DERIVATIVES

This is a 371 of PCT/JP92/00790 filed Jun. 19, 1992, published as WO93/00344, Jan. 7, 1993. This is a continuation of U.S. patent application Ser. No. 08/167,965 filed Dec. 20, 1993, now abandoned.

TECHNICAL FIELD

This invention relates to novel antibiotics having a carbapenem skelton.

BACKGROUND ART

Thienamycin having a carbapenem skelton has been regarded as a promising new antibiotic since its discovery in 1976, because it is effective upon bacterial strains which are resistant against prior art antibiotics and it can exhibit excellent antibacterial activity.

However, thienamycin and various other carbapenem derivatives reported thereafter have to be used as a mixed preparation with a dehydropeptidase (DHP) inhibitor, because they are not only physico-chemically unstable but also apt to be decomposed by DHP and the like enzyme in the kidney, thereby causing side-effects such as renal toxicity.

In addition, an unexamined published Japanese Patent application No. JP-A-60-233076 discloses 1-β-methylcarbapenem compounds which are stable against β-lactamase producing strains, have physico-chemically stable nature and exhibit strong antibacterial activity. These compounds, however, are still unsatisfactory in terms of their stability against DHP and antibacterial activity.

The inventors of the present invention have conducted intensive studies with the aim of finding a carbapenem derivative having more excellent properties and, as a result, have accomplished the present invention by finding a compound which is effective upon various bacterial strains including *Pseudomonas aeruginosa*, excellent in terms of safety and stability against hydrolases such as DHP and the like.

DISCLOSURE OF THE INVENTION

The present invention relates to a carbapenum derivative represented by the following general formula (I), and a salt thereof;

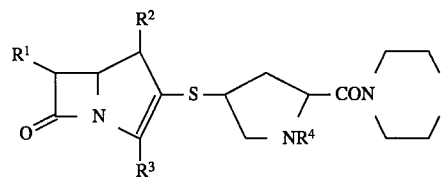

(I)

wherein $R^1$ represents a lower alkyl group or a hydroxy lower alkyl group which may have a protecting group;

$R^2$ represents a hydrogen atom or a lower alkyl group;

$R^3$ represents a carboxyl group which may be esterified;

$R^4$ represents an amino group-protecting group, a hydrogen atom or a lower alkyl group;

$R^5$ and $R^6$, which may be the same or different, each represents a hydrogen atom, a hydroxyl group, a lower alkyl group, a hydroxy lower alkyl group or a halogen atom, and $R^5$ and $R^6$ may together form an alkylene group having 2 to 6 carbon atoms;

$R^7$ represents a hydrogen atom, a lower alkyl group, a carboxyl group, a carbamoyl group, a carboxyl group which may have a protecting group, or a partial structure represented by $—CONR^{71}R^{72}$ where $R^{71}$ and $R^{72}$, which may be the same or different, each represents a hydrogen atom or a lower alkyl group;

$R^8$ represents a hydrogen atom, a lower alkyl group or a hydroxy lower alkyl group, and $R^7$ and $R^8$ may together form an alkylene group having 2 to 6 carbon atoms;

$R^9$ and $R^{10}$, which may be the same or different, each represents an amino group-protecting group, a hydrogen atom or a lower alkyl group;

Z represents a single bond, an oxygen atom, a sulfur atom, or a partial structure represented by $—CR^{11}R^{12}$, $—NR^{13}CO—$, $—CONR^{14}—$ or $—NR^{15}—$ where $R^{11}$ and $R^{12}$ which may be the same or different, each represents a hydrogen atom, a hydroxyl group, a lower alkyl group, a hydroxy lower alkyl group or a halogen atom, and $R^{11}$ and $R^{12}$ may together form an alkylene group having 2 to 6 carbon atoms, $R^{13}$ and $R^{14}$, which may be the same or different, each represents a hydrogen atom or a lower alkyl group and $R^{15}$ represents an amino group-protecting group, a hydrogen atom or a lower alkyl group; and each of m and n represents an integer of 0 to 6.

The term carbapenem as used herein means a compound having the following structural nucleus, and the present invention relates to carbapenem derivatives in which various types of substituent groups are attached to this nucleus.

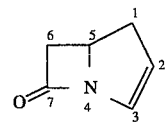

The following describes substituent groups in the general formula (I). In this instance, the term lower alkyl group as used herein means an alkyl group having 1 to 6 carbon atoms (those having 1 to 6 carbon atoms will be expressed respectively as C1–C6 in the following, as well as other cases with different carbon numbers), such as methyl, ethyl, n-propyl, isopropyl, n-butyl and the like.

$R^1$ represents a lower alkyl group or a hydroxyl group-substituted product thereof, namely a hydroxyalkyl group, which may also have a protecting group- Among these, 1-hydroxyethyl group is preferred, especially when 1-hydroxyethyl group is linked to the 6-positioned carbon atom of the carbapenem skeleton in the form of S-configuration and its hydroxyl group is linked to the 1-position of the ethyl group (generally .called the carbapenem 8-position) in the form of R-configuration.

$R^2$ represents a hydrogen atom or a lower alkyl group, preferably a straight- or branched-chain C1–C4 lower alkyl group such as methyl, ethyl or propyl, more preferably a methyl group. In this instance, such groups may preferably have R-configuration with regard to the 1-positioned carbon atom of the carbapenem skeleton.

$R^3$ represents a carboxyl group which may be , esterified. Examples of the ester residue include straight-or branched-chain C1–C6 alkyl groups such as methyl, ethyl, isobutyl or tertiary butyl; C1–C6 alkoxy C1–C6 alkyl groups such as methoxymethyl or methoxyethyl; C2–C7 aliphatic acyloxymethyl groups such as pivaloyloxymethyl; phthalidyl group and the like. Also useful as ester residues which can be removed easily under mild conditions and have a function as a protecting group of carboxyl group include, for example, aralkyl groups such as p-nitrobenzyl, o-nitrobenzyl, benzhydryl or 2-naphthylmethyl, 2,2,2-trichloroethyl group, allyl group ($CH_2=CH—CH_2—$), C1–C6 alkyl substituted silyl groups such as trimethylsilyl, and the like. Examples of ester residues useful as carboxyl group-protecting groups at the time of the synthesis reaction include a p-nitrobenzyl group, an allyl group, and the like. Metabolizable ester residues may also be used, with their preferred examples including a pivaloyloxymethyl group, a phthalidyl group, an acetoxycarbonyloxymethyl group, and the like. Carboxyl group may be in the form of carboxylate anion in relation to other substituent groups, salt, and the like.

$R^4$ represents a hydrogen atom, a straight- or branched-chain C1–C6 lower alkyl group such as methyl, ethyl or propyl, an amino group protecting group which is commonly used in β-lactam antibiotics, such as p-nitrobenzyloxycarbonyl, t-butoxycarbonyl or allyloxycarbonyl, and the like.

$R^5$ and $R^6$, which may be the same or different, each represents a hydrogen atom, a hydroxyl group, a lower alkyl group, a hydroxy lower alkyl group or a halogen atom. In addition, $R^5$ and $R^6$ may together form a polyalkylene chain having 2 to 6 carbon atoms, and form a cyclic structure together with the carbon atom to which $R^5$ and $R^6$ are attached.

$R^7$ represents a hydrogen atom, a lower alkyl group, a carboxyl group, a carbamoyl group, a carboxyl group which may have a protecting group, or a substituted carbamoyl groups represented by the following partial structural formula.

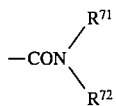

In the above formula, each of $R^{71}$ and $R^{72}$ represents a hydrogen atom or a lower alkyl group. These may together form a polyalkylene chain having 2 to 6 carbon atoms, and form a cyclic structure together with the nitrogen atom to which $R^{71}$ and $R^{72}$ are attached.

$R^8$ represents a hydrogen atom, a lower alkyl group or a hydroxy lower alkyl group. In addition, $R^7$ and $R^8$ may together form a polyalkylene chain having 2 to 6 carbon atoms, and form a cyclic structure together with the carbon atom to which $R^7$ and $R^8$ are attached.

Each of $R^9$ and $R^{10}$ represents an amino group-protecting group, a hydrogen atom or a lower alkyl group. Preferred examples of the amino group-protecting group include those which are usually used in β-lactam antibiotics, for example, p-nitrobenzyloxycarbonyl, t-butoxycarbonyl, allyloxycarbonyl, and the like.

Z represents a single bond or an oxygen atom (—O—) or a sulfur atom (—S—), or a partial structure represented by —$CR^{11}R^{12}$—, —$NR^{13}CO$—, —$CONR^{14}$—. In these formula, $R^{11}$ and $R^{12}$, which may be the same or different, each represents a hydrogen atom, a hydroxyl group, a lower alkyl group, a hydroxy lower alkyl group such as hydroxymethyl or hydroxtethyl, or a halogen atom. In addition, . $R^{11}$ and $R^{12}$ may together form a polyalkylene chain having 2 to 6 carbon atoms, and form a cyclic structure together with the carbon atom to which $R^{11}$ and $R^{12}$ are attached.

Each of $R^{13}$ and $R^{14}$ represents a hydrogen atom or a lower alkyl group.

In addition, $R^{15}$ represents an amino group protecting group, a hydrogen atom or a lower alkyl group. Preferred examples of the amino group protecting group include those which are commonly used in β-lactam antibiotics, for example, p-nitrobenzyloxycarbonyl, t-butoxycarbonyl, allyloxycarbonyl and the like.

Each of m and n is an integer of 0 to 6.

With regard to the configuration of a substituted pyrrolidinylthio group at the 2-positioned substituent of the carbapenem skelton, it is preferable that its bonding area with a carbonyl group at the 2-position is in the form of S-configuration, and the area with a thio group at the 4-position takes S-configuration.

The compound of the present invention and some of the intermediates may have tautomeric structures. Though these structures are shown by a single structural formula in this specification, it should be understood not to be limited thereto.

The compound of the present invention may be used in the form of a pharmacologically acceptable salt. Examples of such salts include carboxylic acid nontoxic salts such as sodium, potassium, aluminium, magnesium and the like metal salts; ammonium salt; triethylamine salt, procaine salt and benzylamine salt, as well as salts with other amines which are commonly used for the salt formation of penicillins and cephalosporins. Among these, sodium salt and potassium salt are particularly preferred. Since the carbapenem derivative of the present invention contains basic substituent, it may also be converted to a pharmacologically acceptable acid addition salt, for example, with an inorganic acid such as hydrochlroic acid, hydrobromic acid, phosphoric acid or sulfuric acid, or with an organic acid such as acetic acid, citric acid, succinic acid, ascorbic acid or methanesulfonic acid. Among these, hydrochloride and sulfate are particularly preferred. The inventive compound may also be used in the form of various solyates such as a hydrate.

Since the compound of the present invention can exhibit excellent antibacterial. property against not only *Escherichia coli, Proteus, Klebsiella, Enterobacter, Salmonella, Serratia, Streptococcus, Staphylococcus* and the like but also *Pseudomonas aeruginosa*, it can be applied efficiently to the treatment of various infectious diseases such as respiratory infection, secondary infection caused by injury lesion, burn injury or operative wound and purulent diseases.

The compound of the present invention can be formulated as pharmaceutical preparations in the usual way formulated with commonly used pharmaceutical additives such as a carrier, a stabilizer, a solubilizing agent and a filler. It may be administered by various routes such as oral administration in the dosage form of tablets, pills, capsules, granules or the like and parenteral administration in the dosage form of intravenous injections, intramuscular injections, suppositories and the like, of which intravenous injection is generally preferable.

In general, it may be administered in an approximate dose of 100 mg to 3 g per adult once a day or dividing the dairy dose into several times. The dose, however, may be changed optionally depending on the age and sex of each patient and symptoms of the disease to be treated.

The compound of the present invention can be produced in accordance with a process represented by the following reaction scheme.

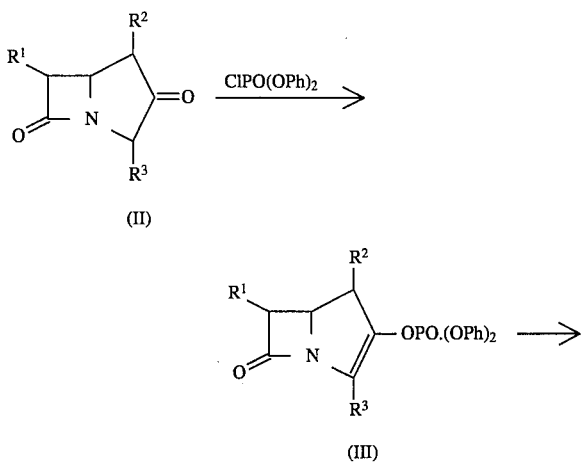

An reactive intermediate (III) can be derived by a reaction of compound (II) ($R^1$, $R^2$ and $R^3$ in the formula are the same groups described in the foregoing) with diphenylphosphoryl chloride according to a known method (D. H. Shih et al., *Heterocycles*, 21, 29 (1984)) or a modified method thereof.

This reaction may be carried out preferably in the presence of an alkylamine such as triethylamine, diisopropylethylamine or the like, an alicyclic amine such as 1,8-diazabicyclo[5.4.0]-7-undecene (DBU), N-methylmorpholine or the like, an organic base such as quinuclidine, 3-quinuclidinol or the like, an inorganic base such as sodium hydroxide, potassium hydroxide, potassium carbonate, sodium carbonate or the like, a metal alkolate such as potassium-t-butoxide, sodium methoxide or the like or sodium amide; among these, diisopropylethylamine or DBU is particularly preferred. Also preferably, this reaction may be carried out in a solvent which does not exert bad influences upon the starting materials and the product, with illustrative examples of the solvent including ketones such as acetone, methylethylketone and the like, acetonitrile, dimethylformamide (DMF), dimethylacetamide, dimethyl sulfoxide (DMSO), tetrahydrofuran (THF), dichloromethane and chloroform, as well as optionally combined mixtures thereof.

The reaction temperature may be in the range of from −50° C. to room temperature, preferably from −40° C. to 0° C. The reaction may be carried out for a period of from 15 minutes to 1 day, preferably from 30 minutes to 8 hours.

The reactLive intermediate (III), after its isolation or as such, is then subjected to a substitution reaction with a thiol compound (IV) to yield the compound (I).

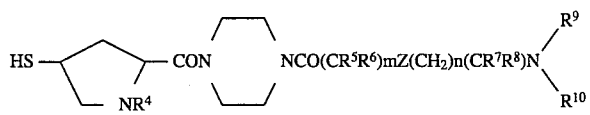

The thiol compound (IV) can be produced by a method of Reference Examples described later. The reaction with the thiol compound (IV) having a high reactivity proceeds well in the presence of a base, though the reaction also progresses without a base. The bases illustrated in the foregoing in relation to the preceding reaction step may also be used in this reaction, of which diisopropylethylamine and DBU are particularly preferred. Such a base may be used preferably in an amount equivalent to the thiol compound, but, when the thiol compound is in the form of an acid addition salt, a good result may be obtained by supplementing an additional amount of the base necessary for the neutralization of the addition acid.

This reaction may also be carried out in a solvent which does not exert bad influences upon the material compounds and the product, and the solvents described in the preceding reaction step may be used as a solvent. When the intermediate (III) is not isolated, it is preferable to continue the reaction in the same solvent.

The compound of formula (iV) may be used in an amount of from 1 to 3 equivalent, preferably from 1 to 2 equivalent, to the compound of formula (III). The reaction temperature may be in the range of from −50° C. to room temperature, preferably from −40° C. to 0° C. The reaction may be carried out for a period of from 30 minutes to 1 day, preferably from 1 to 6 hours. The substitution product can be isolated by usually manner means and, if necessary, purified by subjecting to a silica gel column chromatography using chloroform, ethyl acetate, dichloromethane, methanol or a mixture thereof.

When the substitution reaction product has a protecting group, it can be removed if desired. Its removal may be effected by reductive hydrogenolysis, chemical reduction or hydrolysis using an acid, a base or an enzyme.

When the substituent group $R^3$ in the general formula (I) is esterified and has for example a p-nitrobenzyl group, a benzyl group, a benzhydryl group or a 2-naphthylmethyl group, such a compound can be %ransformed to a carbapenem derivative in which $R^3$ in the general formula (I) is a carboxyl group or a carboxylate anion, by a deprotection reaction through catalytic reduction in the presence of a known metal catalyst such as palladium on charcoal, platinum oxide or the like. More particularly, such a reaction may be carried out in a reaction solvent such as dioxane, THF, water, a buffer solution or a mixture thereof, preferably aqueous dioxane or a mixed solvent consisting of a phosphate buffer and THF, under a hydrogen pressure of from 1 to 5 atmospheric pressure, at a temperature of from 0° to 50° C., preferably from 10° to 30° C., and for a period of from 30 minutes to 16 hours, generally from 10 minutes to 1 hour.

When $R^3$ in the compound (I) is a p-nitrobenzyloxycarbonyl group, it may be allowed to react with ammonium chloride aqueous solution and iron powder in a water soluble organic solvent such as THF or dioxane to yield the compound of interest in which $R^3$ is a carboxyl group or a carboxylate anion, or when $R^3$ is an allyloxycarbonyl group, the compound of interest may be obtained by treating it with tetrakistriphenylphosphinepalladium (0), triphenylphosphine and 2-ethylhexanoic acid in an aprotic solvent such as THF or dichloromethane.

When a protecting group usually used in the synthesis of β-lactam antibiotics such as p-nitrobenzyloxycarbonyl group is applied to the substituent group $R^4$, $R^9$, $R^{10}$ or $R^{15}$ in the general formula (I), such a compound can be converted into a carbapenem derivative in which $R^4$, $R^9$, $R^{10}$ or $R^{15}$ in the general formula (I) is a hydrogen atom, by effecting deprotection reaction through catalytic reduction in the presence of a known metal catalyst such as palladium on charcoal or platinum oxide. The catalytic reduction reaction may be carried out in a solvent such as dioxane, THF, water, a buffer solution or a mixture thereof, preferably aqueous dioxane or a mixed solvent consisting of a phosphate buffer and THF, under a hydrogen pressure of from 1 to 5 atmospheric pressure, at a temperature of from 0° to 50° C., preferably from 10° to 30° C., and for a period of from 30 minutes to 16 hours, generally from 10 minutes to 1 hour, thereby obtaining the carbapenem derivative (I).

When other protecting group usually used in the synthesis of β-lactam antibiotics such as allyloxycarbonyl group is applied to the substituent group $R^4$, $R^9$, $R^{10}$ or $R^{15}$, such a compound can be converted into a carbapenem derivative in which $R^4$, $R^9$, $R^{10}$ or $R^{15}$ in the general formula (I) is a hydrogen atom, by effecting deprotection reaction with tetrakistriphenylphosphinepalladium (0), triphenylphosphine and 2-ethylhexanoic acid in an aprotic solvent such as THF or dichloromethane.

When a plurality of the above protecting groups exist simultaneously on $R^3$, $R^4$, $R^9$, $R^{10}$ and $R^{15}$ in the compound of general formula (I), such a compound can be converted into a carbapenem derivative in which such protecting groups are removed simultaneously, by treating it in accordance with the aforementioned reaction conditions.

The compound of interest can be purified by usually used isolation means, namely by extraction and subsequent concentration, followed, if necessary, by recrystallization, reprecipitation, column chromatography and the like. In addition, the compound (I) can be made into a highly purified form by its crystallization, and such a purpose can be achieved sometimes with a high efficiency when the compound is in a salt form. In that case, the salt is not necessarily a non-toxic acid addition salt, but the compound of interest can be obtained with a high purity by crystallizing it as a toxic salt, purifying the salt and then removing the acid or converting the salt into a pharmacologically acceptable salt.

Esters which is metabolizable in vivo can be produced by making $R^3$ in the compound of general formula (I) into an esterified form in accordance with a means usually used in the synthesis of penicillins and cephalosporins (see for example, *J. Med. Chem.*, 13, 607 (1970)), or by subjecting the carboxyl group or carboxylate anion of the compound to esterification.

BEST MODE OF CARRYING OUT THE INVENTION

The following Inventive and Reference Examples are provided to further illustrate the production process of the compound of the present invention. Abbreviations as used herein mean as follows.

PNZ: p-nitrobenzyloxycarbonyl group
PNB: p-nitrobenzyl group
PMZ: p-methoxybenzyloxycarbony group
PMB: p-methoxybenzyl group
Boc: t-butoxycarbonyl group
Ts: p-toluenesulfonyl group
Ph: phenyl group Unless otherwise specified, the configuration of substituent portions in the following formula (IVa) is a mixture of R and S forms.

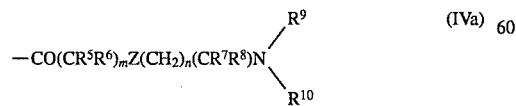

[Reference Example 1]
(2S,4S)-4-mercapto-1-(p-nitrobenzyloxycarbonyl)-2-((1-(2-(p-nitrobenzyloxycarbonyl) aminoacetyl)piperazine-4-yl) carbonyl)pyrrolidine 1) A 3.75 g portion of glycine was dissolved in 25 ml of 2N sodium hydroxide aqueous solution, and to the resulting solution cooled on an ice bath were simultaneously added in dropwise 10.77 g of p-nitrobenzyloxycarbonyl chloride dissolved in ether and 12.5 ml of 4N sodium hydroxide aqueous solution. After stirring at the same temperature for 2 hours, the reaction solution was washed with ether, the resulting aqueous layer was adjusted to acidic with concentrated hydrochloric acid, and the thus precipitated solid material was collected by filtration, washed with water and then dried to yield 11.98 g of N-(p-nitrobenzyloxycarbonyl)glycine as a white solid.
NMR (DMSO-$d_6$) δ: 3.69 (2H, d), 5.20 (2H, s), 7.60 (2H, d), 8.23 (2H, d)

2) A 2.67 g portion of N-p-(nitrobenzyloxycarbonyl)glycine was suspended in 30 ml of dichloromethane, and one drop of dimethylformamide was added to the suspension, followed by 1 hour of reaction at room temperature.
After evaporating the solvent under a reduced pressure, a residue was dissolved again in 25 ml of dichloromethane, and, while cooling at −30° C., 2.63 g of 1-(p-methoxybenzyloxycarbonyl)piperazine and 2.13 g of triethylamine were added to the solution, followed by 2 hours of reaction at room temperature. The reaction solution was mixed with chloroform, washed with water and then dried over sodium sulfate, followed by the removal of solvent by evaporation under a reduced pressure and subsequent addition of n-hexane to the resulting residue to collect a solid material by filtration, thereby obtaining 4.13 g of 1-(p-methoxybenzyloxycarbonyl)-4 -(2-(p-nitrobenzyloxycarbonyl)-aminoacetyl)piperazine.
NMR (CDCl$_3$) δ: 3.2–3.7 (8H, m), 3.80 (3H, s), 4.00 (2H, d), 5.06 (2H, s), 5.18 (2H, s), 6.90 (2H, d), 7.30 (2H, d), 7.48 (2H, d), 8.20 (2H, d)

3) To 3.74 g of 1-(p-methoxybenzyloxycarbonyl)-4-(2-(p-nitrobenzyloxycarbonyl)aminoacetyl)piperazine were added 4.17 ml of anisole and, with cooling on an ice bath, 20 ml of trifluoroacetic acid, followed by 1 hour of reaction at room temperature. After removing trifluoroacetic acid by evaporation under a reduced pressure, the residue was adjusted to basic with a sodium hydroxide aqueous solution and extracted with chloroform, and an organic layer was washed with water and dried over sodium sulfate, followed by removal of the solvent under a reduced pressure and subsequent addition of n-hexane to a residue to collect a solid material by filtration, thereby obtaining 2.45 g of 1-(2-(p-nitrobenzyloxycarbonyl)aminoacetyl)piperazine.
NMR (CDCl$_3$) δ: 2.7–3.0 (4H, m), 3.3–3.5 (2H, m), 3.5–3.7 (2H, m), 4.02 (2H, d), 5.20 (2H, s), 7.50 (2H, d), 8.22 (2H, d)

4) A 1.29 g portion of (2S,4S)-4-benzoylthio-1-(p-nitrobenzyloxycarbonyl)proline was suspended in 10 ml of dichloromethane, and 0.76 g of oxalyl chloride and one drop of dimethylformamide were added to the resulting suspension, followed by 1 hour of stirring. The solvent was removed by evaporation under a reduced pressure, and the resulting residue was dissolved in 10 ml of dichloromethane to which, under cooling on an ice bath, were subsequently added 1.02 g of 1-(2-(p-nitrobenzyloxycarbonyl)aminoacetyl)piperazine and 0.61 g of triethylamine, followed by two nights of reaction at room temperature. The resulting reaction mixture was mixed with chloroform, washed with citric acid aqueous solution, sodium bicarbonate aqueous solution and sodium chloride aqueous solution in that order and then dried over sodium sulfate, followed by evaporation of the solvent under a reduced pressure and subsequent purification of the resulting residue by a silica gel column chromatography to yield a quantitative amount of (2S,4S)-4-benzoylthio-1-(p-nitrobenzyloxycarbonyl) -2-((1-(2-(p-nitrobenzyloxycarbonyl) aminoacetyl)piperazine-4yl)carbonyl)pyrrolidine as a white syrup.

NMR (CDCl$_3$) δ: 1.8–2.2 (1H, m), 2.5–3.0 (1H, m), 3.1–4.4 (13H, m), 4.6–4.9 (1H, m), 5.20 (4H, s), 7.3–7.7 (7H, m), 7.9 (2H, d), 8.22 (4H, d)

5) A 1.47 g portion of (2S,4S)-4-benzoylthio-1-(p-nitrobenzyloxycarbonyl) -2-((1-(2-(p-nitrobenzyloxycarbonyl) aminoacetyl)piperazine-4-yl)carbonyl)pyrrolidine was dissolved in 9 ml of methanol and 6 ml of tetrahydrofuran, and 0.22 g of sodium methoxide was added to the resulting solution with cooling on an ice bath and under an argon stream, followed by 1 hour of reaction. After neutralizing with citric acid aqueous solution and concentrating the solvent, the resulting reaction solution was extracted with chloroform, the thus formed chloroform layer was washed with water and dried over sodium sulfate, the solvent was removed under a reduced pressure and then the resulting residue was subjected to purification using a silica gel column chromatography to yield 1.10 g of the title compound as a white foam.

NMR (CDCl$_3$) δ: 1.8–2.1 (1H, m), 2.5–3.0 (1H, m), 3.0–4.3 (13H, m), 4.5–4.8 (1H, m), 5.20 (4H, s), 7.50 (4H, d), 8.22 (4H, d)

[Reference Example 2]
(2S,4S)-4-mercapto-1-(p-nitrobenzyloxycarbonyl)-2-((1-(2-N,N-dimethylaminoacetyl) piperazine-4-yl)carbonyl)pyrrolidine 1) A 14.9 g portion of (2S,4R)-1-(p-nitrobenzyloxycabonyl) -4-hydoxyproline, 12.4 g of dicyclohexylcarbodiimide and 6.75 g of N-hydroxybenzotriazole were added to 100 ml of tetrahydrofuran, followed by 1 hour of reaction at room temperature to yield an active ester of proline. The reaction product was mixed with 16.5 g of 1-(p-methoxybenzyloxycarbonyl)piperazine and subjected to 2 hours of reaction at room temperature with stirring. After completion of the reaction, a dicyclohexylurea was removed by filtration, the remaining filtrate was evaporated under a reduced pressure, a residue was dissolved in chloroform and washed with 10% citric acid aqueous solution and water, and dried over sodium sulfate, followed by evaporation of the solvent under a reduced pressure to yield an oily residue. This was applied to a silica gel column chromatography and developed with chloroform and a mixture of chloroform and methanol to yield 16.5 g of (2S,4R)-1-(p-nitrobenzyloxycarbonyl) -2-((1-(p-methoxybenzyloxycarbonyl)piperazine-4-yl) carbonyl)-4-hydroxypyrrolidine as the compound of interest.

NMR (CDCl$_3$) δ: 0.90–1.40 (2H, m), 3.00–3.90 (11H, m), 3.80 (3H, s), 4.40–4.70 (1H, m), 4.90–5.44 (4H, m), 6.75–7.02 (2H, m), 7.20–7.60 (4H, m), 8.08–8.30 (2H, m)

2) A 11.8 g portion of triphenylphosphine was dissolved in 200 ml of tetrahydrofuran to which was subsequently added dropwise 7.06 ml of diethyl azodicarboxylate while cooling to −20° C. After 40 minutes of the dropwise addition, to the solution were gradually added dropwise 15.9 g of (2S,4R)-1-(p-nitrobenzyloxycarbonyl) -2-((1-(p-methoxybenzyloxycarbonyl) piperazine-4-yl)carbonyl)-4-hydroxypyrrolidine and 5.2 ml of thiobenzoic acid dissolved in tetrahydrofuran, gradually. After stirring at room temperature over-night, tetrahydrofuran was removed under a reduced pressure, the thus obtained residue was dissolved in ethyl acetate and washed with sodium bicarbonate aqueous solution and the organic layer was washed with water and dried over sodium sulfate, followed by evaporation of the solvent under a reduced pressure. The thus obtained (2S,4S)-4-benzoylthio-1-(p-nitrobenzyloxycarbonyl) -2-((1-(p-methoxybenzyloxycarbonyl) piperazine-4-yl)carbonyl)pyrrolidine was used in the following reaction without subjecting further purification.

3) The crude product obtained above was added to an ice-cooled mixture consisting of 200 ml of trifluoroacetic acid and 50 ml of anisole, followed by 1 hour of reaction at room temperature. After removing trifluoroacetic acid under a reduced pressure, a residue was dissolved in ethyl acetate, neutralized and washed with sodium bicarbonate aqueous solution, washed with water and then dried over sodium sulfate, followed by evaporation of the solvent under a reduced pressure. A residue was applied to a silica gel column chromatography and eluted with a mixture of chloroform and methanol to yield 12 g of (2S,4S)-4-benzoylthio-1-(p-nitrobenzyloxycarbonyl) -2-((piperazine-1-yl)carbonyl)-pyrrolidine.

NMR (CDCl$_3$) δ: 1.8–2.3 (1H, m), 2.6–3.3 (5H, m), 3.3–4.0 (5H, m), 4.0–4.4 (2H, m), 4.6–5.0 (1H, m), 5.23 (2H, s), 7.3–7.7 (5H, m), 7.8–8.0 (2H, m), 8.23 (2H, d)

4) A 0.29 g portion of N,N-dimethylglycine was suspended in 10 ml of dichloromethane, and 0.53 g of oxalyl chloride and one drop of dimethylformamide were added to the mixture, followed by 1 hour of reaction at room temperature. With cooling on an ice bath, to the reaction mixture were added 1.0 g of (2S,4S)-4-benzoylthio-1-(p-nitrobenzyloxycarbonyl)-2 -((piperazine-1-yl)carbonyl)pyrrolidine and 0.63 g of triethylamine, followed by 2 hours of reaction. The reaction solution was mixed with chloroform, washed with water and dried over sodium sulfate, followed by evaporation of the solvent under a reduced pressure and subsequent purification by a silica gel column chromatography to yield 0.49 g of (2S,4S)-4-benzoylthio-1-(p-nitrobenzyloxycarbonyl)-2-((1-(2-N,N-dimethylaminoacetyl) piperazine-4-yl)carbonyl)pyrrolidine as a foam.

NMR (CDCl$_3$) δ: 1.9–2.2 (1H, m), 2.22 (6H, s), 2.5–3.0 (1H, m), 3.10 (2H, s), 3.3–3.9 (8H, m), 3.9–4.4 (3H, m), 4.6–5.0 (1H, m), 5.22 (2H, m), 7.3–7.7 (5H, m), 7.90 (2H, d), 8.20 (2H, d)

5) A 0.49 g portion of (2S,4S)-4-benzoylthio-1-(p-nitrobenzyloxycarbonyl) -2-((1-(2-N,N-dimethylaminoacetyl)-piperazine-4-yl)carbonyl)pyrrolidine was dissolved in a mixture of 10 ml of methanol and 5 ml of tetrahydrofuran, and, with cooling on an ice bath and under an argon gas stream, 0.069 g of sodium methoxide was added to the solution, followed by 60 minutes of reaction. With cooling on an ice bath, the reaction solution was neutralized with 0.076 g of acetic acid and the solvent was concentrated, and a residue was mixed with chloroform, washed with water and dried over sodium sulfate, followed by evaporation of the solvent under a reduced pressure and subsequent purification using a silica gel column chromatography to yield 0.31 g of the title compound as a white foam.

NMR (CDCl$_3$) δ: 1.8–2.1 (1H, m), 2.20 (6H, m), 2.5–3.0 (1H, m), 3.12 (2H, s), 3.2–3.9 (10H, m), 3.9–4.2 (1H, m), 4.5–4.9 (1H, m), 5.20 (2H, s), 7.50 (2H, d), 8.20 (2H, d)

[Reference Example 3]
(2S,4S)-4-mercapto-1-(p-nitrobenzyloxycarbonyl)-2-((1-(4-(p-nitrobenzyloxycarbonyl) aminobutyryl)piperazine-4-yl)carbonyl)pyrrolidine 1) A 3.10 g portion of 4-aminobutyric acid was dissolved in 15 ml of 2N sodium hydroxide, to the solution were simultaneously added dropwise 6.48 g of p-nitrobenzyloxycarbonyl chloride dissolved in ether and 7.5 ml of 4N sodium hydroxide while cooling on an ice-bath. After 2 hours of stirring at the same temperature, the solution was washed with ether, the resulting aqueous layer was adjusted to acidic with concentrated hydrochloric acid, and a precipitated. solid material was collected by filtration, washed with water and then dried to yield 7.64 g of 4-(p-nitrobenzyloxycarbonyl)aminobutyric acid.

NMR (DMSO-$d_6$) δ: 1.5–1.9 (2H, m), 2.28 (2H, t), 3.04 (2H, q), 5.18 (2H, s), 7.62 (2H, d), 8.25 (2H, d)

2) To 1.13 g of 4-p-(nitrobenzyloxycarbonyl)aminobutyric acid dissolved in tetrahydrofuran were added, with cooling on an ice bath, 0.48 g of N-hydroxysuccunimide and 0.87 g of dicyclohexylcarbodiimide, followed by overnight reaction with stirring. To the solution were added 1.0 g of 1-(p-methoxybenzyloxycarbonyl)piperazine and 0.41 g of triethylamine, followed by 2 hours of reaction. After removal of an insoluble material from the reaction mixture by filtration and subsequent concentration of the filtrate, the thus obtained residue was mixed with ethyl acetate, washed with sodium bicarbonate aqueous solution, citric acid aqueous solution and sodium chloride aqueous solution in that order and then dried over sodium sulfate, followed by evaporation of the solvent under a reduced pressure. Thereafter, the resulting residue was subjected to a silica gel column chromatography to yield 1.49 g of 1-(p-methoxybenzyloxy-carbonyl) -4-(4-(p-nitrobenzyloxycarbonyl)aminobutyryl)piperazine.

NMR (CDCl$_3$) δ: 1.5–2.1 (2H, m), 2.40 (2H, t), 3.1–3.7 (10H, m), 3.80 (3H, s), 5.08 (2H, s), 5.20 (2H, s), 6.90 (2H, d), 7.30 (2H, d), 7.50 (2H, d), 8.20 (2H, d)

3) A 0.86 g portion of (2S,4S)-4-benzoylthio-1-(p-nitrobenzyloxycarbonyl)proline was suspended in 10 ml of dichloromethane, and 0.51 g of oxalyl chloride and one drop of dimethylformamide were added to the suspension, followed by 1 hour of reaction at room temperature. With cooling on an ice bath, to the solution were added 0.74 g of 1-(4-(p-nitrobenzyloxycarbonyl)aminobutyryl)piperazine and 0.41 g of triethylamine, followed by 3 hours of reaction at room temperature. The resulting reaction mixture was mixed with chloroform, washed with sodium bicarbonate aqueous solution, citric acid aqueous solution and sodium chloride aqueous solution in that order and then dried over sodium sulfate, followed by evaporation of the solvent under a reduced pressure. Thereafter, a residue was subjected to a silica gel column chromatography to yield 1.64 g of foamy (2S, 4S)-4-benzoylthio -1-(p-nitrobenzyloxycarbonyl)-2-((1-(4-(p-nitrobenzyloxycarbonyl) aminobutyryl)piperazine-4-yl)carbonyl)pyrrolidine.

NMR (CDCl$_3$) δ: 1.5–2.1 (3H, m), 2.2–2.5 (2H, m), 2.5–4.4 (14H, m), 4.5–4.9 (1H, m), 5.20 (2H, s), 5.25 (2H, s), 7.3–7.7 (7H, m), 7.90 (2H, d), 8.20 (4H, d)

4) A 1.53 g portion of (2S,4S)-4-benzoylthio-1-(p-nitrobenzyloxycarbonyl) -2-((1-(4-(p-nitrobenzyloxycarbonyl)aminobutyryl) piperazine-4-yl)carbonyl)pyrrolidine was dissolved in a mixture of 20 ml of methanol and 10 ml of tetrahydrofuran, and 0.16 g of sodium methoxide was added to the solution with cooling on an ice bath, followed by 1 hour of reaction. With cooling on an ice bath, the mixture was neutralized with citric acid aqueous solution and concentrated, and a residue was dissolved in chloroform, washed with water and dried over sodium sulfate, followed by evaporation of the solvent under a reduced pressure and subsequent treatment of a residue with a silica gel column chromatography to yield a quantitative amount of the title compound.

NMR (CDCl$_3$) δ: 1.5–2.1 (3H, m), 2.2–2.5 (2H, m), 2.5–3.0 (1H, m), 3.0–4.2 (13H, m), 4.5–4.8 (1H, m), 5.20 (2H, s), 5.22 (2H, s), 7.50 (4H, d), 8.20 (4H, d) ,

[Reference Example 4]

(2S,4S)-4-mercapto-1-(p-nitrobenzyloxycarbonyl)-2-((1-((2S)-(4-(p-nitrobenzyloxycarbonyl) amino-2-hydroxybutyryl)-piperazine-4-yl)carbonyl)pyrrolidine 1) A 2.82 g portion of (2S)-4-amino-2-hydroxybutyric acid was dissolved in 15 ml of 2N sodium hydroxide, and to the solution cooled on an ice bath were simultaneously added dropwise 6.13 g of p-nitrobenzyloxycarbonyl chloride dissolved in ether and 7.5 ml of 4N sodium hydroxide. After 2 hours of stirring at the same temperature, the solution was washed with ether, an aqueous layer was adjusted to acidic with concentrated hydrochloric acid, and a precipitated solid material was collected by filtration, washed with water and then dried to yield 4.48 g of (2S)-4-(p-nitrobenzyloxycarbonyl) amino-2-hydroxybutyric acid.

NMR (DMSO-$d_6$) δ: 1.5–2.1 (2H, m), 2.9–3.4 (2H, m), 3.99 (1H, dd), 5.16 (2H, s), 7.59 (2H, d), 8.23 (2H, d)

2) To 0.9 g of (2S)-4-(p-nitrobenzyloxycarbonyl)amino-2-hydroxybutyric acid dissolved in tetrahydrofuran were added, with cooling on an ice bath, 0.36 g of N-hydroxysuccunimide and 0.65 g of dicyclohexylcarbodiimide, followed by overnight reaction with stirring. To the solution were added 0.75 g of 1-(p-methoxybenzyloxycarbonyl)piperazine and 0.31 g of triethylamine, followed by 2 hours of reaction. After removal of insoluble material from the reaction mixture by filtration and subsequent concentration of the filtrate, a residue was mixed with ethyl acetate, washed with sodium bicarbonate aqueous solution, citric acid aqueous solution and sodium chloride aqueous solution in that order and then dried over sodium sulfate, followed by evaporation of the solvent under a reduced pressure. Thereafter, the resulting residue was subjected to a silica gel column chromatography to yield 1.33 g of 1-(p-methoxybenzyloxycarbonyl)-4-((2S)-(4-(p-nitrobenzyloxycarbonyl) amino-2-hydroxybutyryl)piperazine.

NMR (CDCl$_3$) δ: 1.5–2.1 (2H, m), 3.2–3.8 (4H, m), 3.80 (3H, s), 4.3–4.5 (1H, m), 5.06 (2H, s), 5.18 (2H, s), 6.90 (2H, d), 7.30 (2H, d), 7.48 (2H, d), 8.20 (2H, d)

3) A 1.32 g of 1-(p-methoxybenzyloxycarbonyl)-4-((2S)-4-(p-nitrobenzyloxycarbonyl) amino-2-hydroxybutyryl)piperazine was added to a mixture of 15 ml of trifluoroacetic acid and 1.35 ml of anisole, followed by 1 hour of reaction at room temperature. After removing trifluoroacetic acid by evaporation under a reduced pressure, a residue was adjusted to basic with sodium hydroxide and extracted with chloroform, and the organic layer was washed with water and dried over sodium sulfate, followed by evaporation of the solvent under a reduced pressure. Thereafter, the resulting residue was subjected to a silica gel column chromatography to yield 0.91 g of 1-((2S)-4-(p-nitrobenzyloxycarbonyl)amino-2-hydroxybutyryl)piperazine as a syrup.

NMR (CDCl$_3$) δ: 1.5–2.3 (2H, m), 2.4–3.1 (4H, m), 3.2–3.8 (6H, m), 4.42 (1H, dd), 5.20 (2H, s), 7.50 (2H, d), 8.22 (2H, d)

4) A 1.04 g portion of (2S,4S)-4-benzoylthio-1-(p-nitrobenzyloxycarbonyl)proline was dissolved in 20 ml of tetrahydrofuran, and, with cooling on an ice bath, 0.55 g of N-hydroxybenzotriazole and 1.49 g of dicyclohexylcarbodiimide were added to the solution, followed by 1 hour of reaction with stirring at room temperature. To the solution were added 0.88 g of 1-((2S)-4-(p-nitrobenzyloxycarbonyl)amino-2-hydroxybutyryl)piperazine and 0.49 g of triethylamine, followed by 1 hour of reaction at room temperature. After concentration of the solvent, the residue was mixed with ethyl acetate to remove insoluble material, washed with sodium bicarbonate aqueous solution, citric acid aqueous solution and sodium chloride aqueous solution in that order and then dried over sodium sulfate, followed by evaporation of the solvent under a reduced pressure. Thereafter, the resulting residue was subjected to a silica gel column chromatography to yield 1.80 g of (2S,4S)-4-benzoylthio-1-(p-nitrobenzyloxycarbonyl) -2-((1-((2S)-4-(p-nitrobenzyloxycarbonyl) amino-2-hydroxybutyryl)piperazine-4-yl)carbonyl)pyrrolidine.

NMR (CDCl$_3$) δ: 1.5–2.2 (3H, m), 2.5–4.6 (15H, m), 4.7–5.0 (1H, m), 5.18 (2H, s), 5.24 (2H, s), 7.48 (7H, d), 7.92 (2H, d), 8.20 (4H, d)

5) A 1.56 g portion of (2S,4S)-4-benzoylthio-1-(p-nitrobenzyloxycarbonyl) -2-((1-((2S)-4-(p-nitrobenzyloxycarbonyl) amino-2-hydroxybutyryl)piperazine-4-yl)carbonyl)pyrrolidine was dissolved in a mixture of 10 ml of methanol and 10 ml of tetrahydrofuran, and 0.32 g of sodium methoxide was added to the resulting solution with cooling on an ice bath and under an argon stream, followed by 1 hour of reaction. With cooling on an ice bath, the reaction mixture was neutralized with citric acid aqueous solution and the solvent was concentrated, and the residue was dissolved in ethyl acetate, washed with water and dried over sodium sulfate, followed by evaporation of the solvent under a reduced pressure. Thereafter, the resulting residue was subjected to a silica gel column chromatography to yield 1.25 g of the title compound in pale yellow color.

NMR (CDCl$_3$) δ: 1.5–2.1 (2H, m), 2.2–2.9 (2H, m), 3.0–4.3 (13H, m), 4.3–4.6 (1H, m), 4.6–4.9 (1H, m), 5.20 (4H, s), 7.52 (4H, d), 8.24 (4H, d)

The following shows substituent groups of the structural part represented by (IVa) in the compounds (IV) obtained in the above Reference Examples, substituent groups of the structural part represented by (IVa) in other compounds (IV) obtained in the same manner and results of their NMR analysis. Unless otherwise noted, $R^4$ is a p-nitrobenzyloxycarbonyl group.

Compound IV-1: Z=single bond, m=n=0, $R^7$=$R^8$=H, $R^9$=PNZ, $R^{10}$=H,

Compound IV-2: Z=single bond, m=n=0, $R^7$=$R^8$=H, $R^9$=$R^{10}$=CH$_3$,

Compound IV-3: Z=single bond, m=0, n=2, $R^7$=$R^8$= H, $R^9$=PNZ, $R^{10}$=H,

Compound IV-4: Z=single bond, $R^5$=H, $R^6$=OH, m=n=1, $R^7$= $R^8$=H, $R^9$=PNZ, $R^{10}$=H, 2S, Compound IV-5: Z=single bond, m=n=0, $R^7$=CH$_3$, $R^8$=H, $R^9$= PNZ, $R^{10}$=H, 2R, 1.36 (3H, d), 2.4–2.9 (1H, m), 3.1–4.2 (11H, m), 4.5–4.9 (2H, m), 5.20 (4H, s), 7.50 (4H, d), 8.22 (4H, d)

Compound IV-6: Z=single bond, m=n=0, $R^7$=CH$_3$, $R^8$=H, $R^9$=PNZ, $R^{10}$=H, 2S, 1.36 (3H, d), 2.4–3.0 (1H, m), 3.0–4.3 (11H, m), 4.5–4.9 (2H, m), 5.20 (4H, s), 7.50 (4H, d), 8.22 (4H, d)

Compound IV-7: Z=single bond, m=n=0, $R^7$=$R^8$H, $R^9$=CH$_3$, $R^{10}$32 PNZ, 1.8–2.1 (1H, m), 2.5–3.0 (1H, m), 3.05 (3H, s), 3.2–3.9 (11H, m), 4.06 (2H, m), 4.70 (1H, t), 5.20 (2H, s), 5.24 (2H, s), 7.50 (4H, d), 8.20 (4H, d)

Compound IV-8: Z=single bond, m=n=0, $R^7$=$R^8$=CH$_3$, $R^9$=PNZ, $R^{10}$=H, 1.59 (6H, s), 1.80–2.00 (1H, m), 2.4–2.9 (1H, m), 3.0–3.9 (10H, m), 4.0–4.2 (2H, m), 4.5–4.8 (1H, m), 5.18 (2H, s), 5.22 (2H, s), 7.51 (4H, d), 8.22 (4H, d)

Compound IV-9: Z=single bond, m=n=0, $R^7$+$R^8$=—(CH$_2$)$_2$—, $R^9$=PNZ, $R^{10}$=H, 0.95–1.40 (4H, m), 1.75–2.13 (1H, m), 2.50–3.00 (1H, m), 3.10–3.90 (9H, m), 4.00–4.20 (2H, m), 4.50–4.90 (1H, m), 5.00–5.30 (4H, m), 7.50 (4H, d), 8.20 (4H, d)

Compound IV-10: Z=single bond, m=0, n=1, $R^7$=$R^8$=H, $R^9$=PNZ, $R^{10}$=H, 1.7–2.1 (1H, m), 2.4–3.0 (3H, m), 3.0–4.2 (13H, m), 4.65 (1H, t), 5.20 (2H, s), 5.25 (2H, s), 7.50 (4H, d), 8.20 (4H, d).

Compound IV-11: Z=single bond, m=n=0, $R^7$=H, $R^8$=CH$_2$OH, $R^9$=PNZ, $R^{10}$H, 2R, 2.4–2.9 (1H, m), 3.0–4.2 (13H, m), 4.5–4.9 (2H, m), 5.21 (4H, s), 7.50 (4H, d), 8.22 (4H, d)

Compound IV-12: Z=single bond, m=n=0, $R^7$=H, $R^8$ CH$_2$OH, $R^9$PNZ, $R^{10}$=H, 2S, 2.65–2.80 (1H, m), 3.0–4.2 (13H, m), 4.6–4.75 (2H, m), 5.15–5.25 (4H, m), 7.50 (2H, d), 7.51 (2H, d), 8.22 (2H, d), 8.23 (2H, d)

Compound IV-13: Z=single bond, $R^5$H, $R^6$=OH, m=1, n=0, $R^7$=$R^8$=H, R $^9$=PNZ, $R^{10}$= H, 2S, 1.6–3.0 (2H, m), 3.0–4.3 (13H, m), 4.3–4.9 (2H, m), 5.20 (4H, s), 7.50 (4H, d), 8.20 (4H, d)

Compound IV-14: Z=single bond, $R^5$=H, $R^6$=F, m=1, n=0, $R^7$=$R^8$=H, $R^9$=PNZ, $R^{10}$=H, 2R, 1.90–2.30 (1H, m), 2.50–3.05 (1H, m), 3.05–4.00 (11H, m), 4.00–4.45 (2H, m), 4.60–5.70 (6H, m), 7.50 (4H, d), 8.22 (4H, d), Compound IV-15: Z=single bond, m=0, n=2, $R^7$=H, $R^8$=CH$_2$OH, $R^9$=PNZ, $R^{10}$=H, 4S, 1.40–2.20 (3H, m), 2.20–2.60 (2H, m), 2.60–3.10 (1H, m), 3.10–3.90 (13H, m), 3.90–5.30 (7H, m), 7.50 (4H, d), 8.10–8.33 (4H, m)

Compound IV-16: Z=CR$^{11}$R$^{12}$, $R^5$=$R^6$=H, m=2, n=0, $R^7$=$R^8$H =H, $R^9$PNZ, $R^{10}$=H, $R^{11}$=H, $R^{12}$=CH$_3$, 1.21 (3H, d), 1.60–2.53 (5H, m), 2.53–3.96 (11H, m), 3.96–5.00 (3H, m), 5.16 (2H, m), 5.23 (2H, m), 7.30–7.80 (4H, m), 8.05–8.24 (4H, m)

Compound IV-17: Z=CR$^{11}$R$^{12}$, $R^5$=$R^6$=H, m=1, n=0, $R^7$=$R^8$=H, $R^9$=PNZ, $R^{10}$=H, $R^{11}$=H, $R^{12}$=OH, 2.3–2.5 (2H, m), 2.5–2.9 (1H, m), 3.0–3.9 (12H, m), 3.9–4.25 (2H, m), 4.5–4.8 (1H, m), 5.21 (4H, s), 7.51 (4H, d), 8.22 (4H, d)

Compound IV-18: Z=single bond, $R^5$=H, $R^6$OH, m=1, n=2, $R^7$=$R^8$=H, , $R^9$=PNZ, $R^{10}$=H, 2S, 1.2–2.3 (5H, m), 2.5–4.5 (15H, m), 4.5–4.8 (1H, m), 5.20 (2H, m), 7.50 (4H, d), 8.20 (4H, d)

Compound IV-19: Z=single bond, m0, n=3, $R^7$=$R^8$H, $R^9$=PNZ, $R^{10}$=H, 1.3–2.0 (5H, m), 2.1–2.5 (2H, m), 2.5–3.0 (1H, m),3.0–4.3 (13H, m), 4.5–4.8 (1H, m), 5.20 (4H, s), 7.50 (4H, d), 8.20 (4H, d)

Compound IV-20: Z=single bond, m=0, n=4, $R^7$=$R^8$= H, $R^9$=PNZ, $R^{10}$H, 1.0–2.1 (7H, m), 2.1–2.4 (2H, m), 2.5–4.2 (14H, m), 4.5–4.9 (1H, m), 5.20 (2H, s), 5.23 (2H, s), 7.50 (4H, d), 8.20 (4H, d)

(In each of the above compounds IV-4, IV-5, IV-6, IV-11, IV-12, IV-13, IV-14, IV-15 and IV-18, configuration in the partial structure of (IVa) is shown together with a numeral which indicates the position number of corresponding atom in the partial structure of (IVa) when the carbon atom of carbonyl group (carbonyl carbon) is defined as the 1-position.)

[Inventive Example 1]

(1R,5S,6S,8R,2'S,4'S)-2-((2-((1-(2-aminoacetyl)piperazine-4-yl) carbonyl)pyrrolidine-4-yl)thio)-6-(1-hydroxyethyl)-1-methylcarbapenem-3-carboxylic acid 1) To 0.2 g of p-nitrobenzyl (1R,5S,6S,8R)-6-(1-hydroxyethyl) -1-methyl-2-oxocarbapenam-3-carboxylate dissolved in acetonitrile were added 83 mg of diisopropylethylamine and 173 mg of diphenylphosphoryl chloride in that order under an argon gas stream at 0° C., followed by 1 hour of reaction at the same temperature. After cooling down to −35° C., to this were added 80 mg of diisopropylethylamine and 390 mg of (2S,4S)-4-mercapto-1-(p-nitrobenzyloxycarbonyl) -2-((1-(2-(p-nitrobenzyloxycarbonyl)-aminoacetyl) piperazine-4-yl)carbonyl)pyrrolidine in that order, followed by 2 hours of reaction at the same temperature. After concentration of the reaction solution, the residue was mixed with chloroform, washed with sodium bicarbonate aqueous solution, citric acid aqueous solution and water in that order and then dried over sodium sulfate, followed by evaporation of the solvent under a reduced pressure. The resulting residue was then subjected to purification by a silica gel column chromatography to yield 416 mg of p-nitrobenzyl (1R,5S,6S,8R,2'S,4'S)-2-((1-(p-nitrobenzyloxycarbonyl) -2-((2-(p-nitrobenzyloxycarbonyl) aminoacetyl)piperazine-4-yl)carbonyl)pyrrolidine-4-yl)thio) -6-(1-hydroxyethyl)-1-methylcarbapenem-3-carboxylate as a yellow foam.

NMR (CDCl$_3$) δ: 1.0–1.4 (6H, m), 1.6–2.1 (1H, m), 2.5–3.0 (1H, m), 4.5–4.8 (1H, m), 5.0–5.6 (6H, m), 7.3–7.8 (6H, m), 8.22 (6H, d)

2) A 416 mg portion of the compound obtained in the above step 1) was suspended in a mixture of 8 ml of tetrahydrofuran and 8 ml of phosphate buffer, and 3 hours of hydrogenation was carried out in the presence of 150 mg of platinum oxide under 5 atmospheric pressure. After removing the catalyst by filtration and removing tetrahydrofuran by evaporation under a reduced pressure, a residue was subjected to purification by a column chromatography using Diaion HP-20, followed by further purification by HPLC, thereby yielding 21.1 mg of the title compound.

NMR (D$_2$O) δ: 1.23 (3H, d), 1.32 (3H, d), 1.6–1.7 (1H, m), 2.65– 2.85 (1H, m), 3.0–3.1 (1H, m), 3.1–3.2 (1H, m), 3.3–3.4 (2H, m), 3.5–3.9 (1H, m), 4.05–4.15 (1H, m), 4.15–4.30 (2H, m)

[Inventive Example 2]

(1R,5S,6S,8R,2'S,4'S)-2-((2-((1-((2-N,N-dimethylaminoacetyl) piperazine-4-yl)carbonyl)pyrrolidine-4-yl) thio)-6-((1-hydroxyethyl)-1-methylcarbapenem-3-carboxylic acid 1) To 199 mg of p-nitrobenzyl (1R,5S,6S,8R)-6-(1-hydroxyethyl)-1 -methyl-2-oxocarbampenam-3-carboxylate dissolved in acetonitrile were added 85 mg of diisopropylethylamine and 177 mg of diphenylphosphoryl chloride in that order under an argon gas stream on an ice bath, followed by 1 hour of reaction at the same temperature. After cooling down to −35° C., to the solution were added 82 mg of diisopropylethylamine and 303 mg of (2S,4S)-4-mercapto-1-(p-nitrobenzyloxycarbonyl) -2-((1-(N,N-dimethylglycyl)-piperzine-4-yl) carbonyl)pyrrolidine in that order, followed by 2 hours of reaction at the same temperature. After concentration of the solvent, the resulting residue was dissolved in chloroform, washed with water and then dried over sodium sulfate, followed by evaporation of the solvent under a reduced pressure. The resulting residue was then subjected to purification by a silica gel column chromatography to yield 429 mg of foamy p-nitrobenzyl (1R,5S,6S,8R,2'S,4'S)-2-((1-(p-nitrobenzyloxycarbonyl)-2-(1((2-N,N -N,N-dimethylaminoacetyl)piperazine-4-yl)carbonyl)-pyrrolidine -4-yl)thio)-6-(1-hydroxyethyl)-1-methylcarbapenem-3-carboxylate.

NMR (CDCl$_3$) δ: 1.0–1.4 (6H, m), 1.7–2.3 (7H, m), 2.5–4.4 (14H, m), 4.5–4.8 (1H, m), 5.0–5.6 (4H, m), 7.4–7.7 (4H, m), 8.20 (4H, d)

2) A 42:9 mg portion of p-nitrobenzyl (1R,5S,6S,8R,2'S,4'S)-2-((1-(p-nitrobenzyloxycarbonyl)-2-(1-((2 -N,N-dimethylaminoacetyl)piperazine-4-yl) carbonyl)pyrrolidine-4-yl)thio)-6-(1-hydroxyethyl)-1 -methylcarbapenem-3-carboxylate obtained in the above step 1) was suspended in a mixture of 10 ml of tetrahydrofuran and 10 ml of phosphate buffer, and 2 hours of hydrogenation was carried out in the presence of 150 mg of platinum oxide under 5 atmospheric pressure. After removing the catalyst by filtration and removing tetrahydrofuran by evaporation under a reduced pressure, the residue was subjected to purification by a column chromatography using Diaion HP-20, and the fraction of interest was further purified by HPLC, thereby yielding 18.3 mg of the title compound.

NMR (D$_2$O) δ: 1.22 (3H, d), 1.30 (3H, d), 1.65–1.75 (1H, m), 2.75– 2.85 (1H, m), 2.87 (6H, s), 3.10–3.20 (1H, m), 3.27(1H, dd), 3.35–3.55 (2H, m), 3.50–360(2H, m), 3.60–3.75 (6H, m), 3.80≡3.90 (1H, m), 4.15–4.30 (5H, m)

[Inventive Example 3]

(1R,5S,6S,8R,2'S,4'S)-2-((2-((1-(4-aminobutyryl)piperazine-4-yl) carbonyl)pyrrolidine-4-yl)thio)-6-(1-hydroxyethyl)-1-methylcarbapenum -3-carboxylic acid 1) To 199 mg of p-nitrobenzyl (1R,5S,6S,8R)-6-(1 -hydroxyethyl)-1-methyl-2-oxocarbapenam-3-carboxylate dissolved in acetonitrile were added dropwise 85 mg of diisopropylethylamine and 177 mg of diphenylphosphoryl chloride in that order under an argon gas stream at 0° C., followed by 1 hour of reaction at the same temperature. After cooling down to −35° C., to the solution were added 82 mg of diisopropylethylamine and 416 mg of (2S,4S)-4-mercapto-1-(p-nitrobenzyloxycarbonyl) -2-((1-(4-(p-nitrobenzyloxycarbonyl) aminobutyryl)piperazine-4-yl)carbonyl)pyrrolidine in that order, followed by 2 hours of reaction at the same temperature. After concentration of the solvent, the resulting residue was mixed with chloroform, washed with sodium bicarbonate aqueous solution, citric acid aqueous solution and sodium chloride aqueous solution in that order and then dried over sodium sulfate, followed by evaporation of the solvent under a reduced pressure and subsequent application of the resulting residue to a silica gel column chromatography to yield 489 mg of p-nitrobenzyl (1R,5S,6S,8R,2'S,4'S)-2-((1-(p-nitrobenzyloxycarbonyl)-2-((1 -(4-(p-nitrobenzyloxycarbonyl)aminobutyryl)piperazine-4-yl) carbonyl/pyrrolidine-4-yl)thio)-6-(1-hydroxyethyl)-1-methylcarbapenum -3-carboxylate.

NMR (CDCl$_3$) δ: 1.0–1.4 (6H, m), 1.5–2.1 (3H, m), 2.1–3.0 (3H, m), 3.0–4.4 (17H, m), 4.5–4.9 (1H, m), 5.0–5.6 (6H, m), 7.3–7.8 (6H, m), 8.20 (6H, d)

2) A 477 mg portion of the compound obtained in the above step was suspended in a mixture of 10 ml of tetrahydrofuran and 10 ml of phosphate buffer, and 2 hours of hydrogenation was carried out in the presence of 150 mg of platinum oxide under 5 atmospheric pressure. After removing the catalyst by filtration and removing tetrahydrofuran by evaporation under a reduced pressure, the thus residue was subjected to purification by a column chromatography using Diaion HP-20, followed by further purification of the fraction of interest by HPLC, thereby yielding 50.7 mg of the title compound.

NMR (D$_2$O) δ: 1.21 (3H, d), 1.30 (3H, d), 1.6–1.7 (1H, m), 1.8– 1.9 (2H, m), 2.5–2.6 (2H, m), 2.6–2.8 (1H, m), 2.9–3.0 (3H, m), 3.0–3.1 (1H, m), 3.3–3.4 (2H, m), 3.5–3.7 (6H, m), 3.7–3.8 (1H, m), 4.1–4.3 (3H, m)

[Inventive Example 4]

(1R,5S,6S,8R,2'S,4'S)-2-((2-((1-((2S)-4-amino-2 -hydroxybutyryl)piperazine-4-yl)carbonyl)pyrrolidine-4-yl) thio)-6-(1-hydroxyethyl)-1-methylcarbapenem-3-carboxylic acid 1) To 204 mg of p-nitrobenzyl (1R,5S,6S,8R)-6-(1-hydroxyethyl)-1-methyl-2-oxocarbapenam-3-carboxylate dissolved in acetonitrile were added 80 mg of diisopropylethylamine and 166 mg of diphenylphosphoryl chloride in that order under an argon gas stream at 0° C., followed by 1 hour of reaction at the same temperature. After cooling down to −35° C., to the solution were added 80 mg of diisopropylethylamine and 418 mg of (2S,4S)-4-mercapto-1-(p-nitrobenzyloxycarbonyl)-2-((1-((2S)-4-(p-nitrobenzyloxycarbonyl) amino-2-hydroxybutyryl)piperazine-4-yl)carbonyl)pyrrolidine in that order, followed by 5 hours of reaction at the same temperature. After concentration of the solvent, the resulting residue was dissolved in chloroform, washed with water and then dried over sodium sulfate, followed by evaporation of the solvent under a reduced pressure and subsequent purification of the resulting residue by a silica gel column chromatography to yield 468 mg of p-nitrobenzyl (1R,5S,6S,8R,2'S,4'S)-2-((1-(p-nitrobenzyloxycarbonyl)-2-((1((1-((2S-4(p-nitrobenzyloxycarbonyl)amino-2-hydroxybutyryl) piperazine-4-yl)carbonyl)pyrrolidine-4-yl) thio)-6-(1-hydroxyethyl)-1-methylcarbapenem-3-carboxylate.

NMR (CDCl$_3$) δ: 1.0–1.4 (6H, m), 1.4–2.2 (3H, m), 2.4–2.9 (1H, m), 3.0–4.5 (18H, m), 4.5–4.9 (1H, m), 5.20 (4H, s), 5.38 (2H, q), 7.50 (4H, d), 7.63 (2H, d)

2) A 468 mg portion of the compound obtained in the above step was suspended in a mixture of 7 ml of tetrahydrofuran and 7 ml of phosphate buffer, and 4 hours of hydrogenation was carried out in the presence of 300 mg of 10% palladium-carbon under 4 atmospheric pressure. After removing the catalyst by filtration and removing tetrahydrofuran by evaporation under a reduced pressure, the residue was subjected to a column chromatography using Diaion HP-20, followed by further purification of the fraction of interest by HPLC, thereby yielding 11 mg of the title compound.

NMR (D$_2$O) δ: 1.24 (3H, d), 1.33 (3H, d), 1.6–1.7 (1H, m), 1.90–2.05 (1H, m), 2.05–2.15 (1H, m), 2.70–2.85 (1H, m), 3.05–3.15 (1H, m), 3.15–3.25 (3H, m), 3.40–3.50 (2H, m), 3.6–3.9 (9H, m), 4.15–4.30 (3H, m), 4.75–4.85 (1H, m)

The following shows substituent groups represented by (IVa) of the compounds (I) obtained in the above Inventive Examples, substituent groups represented by (IVa) of other compounds obtained in the same manner and results of their NMR analysis. In these compounds, $R^1$ is 1-hydroxyethyl (6S,8R) and $R^2$ is methyl (1R).

Compound I-1: Z=single bond, m=n=0, $R^7=R^8=R^9=R^{10}=H$,

Compound I-2: Z=single bond, m=n=0, $R^7=R^8=H$, $R^9=R^{10}=CH_3$,

Compound I-3: Z=single bond, m=0, n=2, $R^7=R^8=R^9=R^{10}H$,

Compound I-4: Z=single bond, $R^5=H$, $R^6=OH$, m=n=1, $R^7=R^8=R^9=R^{10}=H$, 2S, Compound I-5: Z=single bond, m=n=0, $R^7=CH_3$, $R^8=R^9=R^{10}=H$, 2R, 1.22 (3H, d), 1.30 (3H, d), 1.44 (3H, dd), 1.63–1.69 (1H, m), 2.75–2.82 (1H, m), 3.11 (1H, m), 3.21 (1H, dd), 3.37–3.45 (2H, m), 3.61–3.75 (8H, m), 3.81–3.88 (1H, m), 4.17–4.29 (3H, m), 4.35–4.44 (1H, m)

Compound I-6: Z=single bond, m=n=0, $R^7=CH_3$, $R^8=R^9=R^{10}=H$, 2S, 1.22 (3H, d), 1.30 (3H, d), 1.47 (3H, dd), 1.68–1.72 (1H, m), 2.76–2.85 (1H, m), 3.15 (1H, m), 3.28 (1H, dd), 3.35–3.45 (2H, m), 3.60–3.78 (8H, m), 3.83–3.91 (1H, m), 4.21–4.31 (3H, m), 4.45 (1H, m)

Compound I-7: Z=single bond, m=n=0, $R^7=R^8=H$, $R^9=CH_3$, $R^{10}=H$ 1.21 (3H, d), 1.30 (3H, d), 1.6–1.7 (1H, m), 2.7–2.8 (4H, m), 3.10 (1H, d), 3.21 (1H, dd), 3.4–3.5 (2H, m), 3.5–3.6 (2H, m), 3.6–3.7 (6H, m), 3.8–3.9 (1H, m), 4.10 (2H, d), 4.1–4.3 (3H, m), Compound I-8: Z=single bond, m=n=0, $R^7$, =$R^8$=$CH_3$, $R^9=R^{10}=H$, 1.22 (3H, d), 1.30 (3H, d), 1.63–1.74 (1H, m), 1.70 (6H, s), 2.73–2.80 (1H, m), 3.12 (1H, dd), 3.22 (1H, dd), 3.36–3.45 (2H, m), 3.63–3.88 (9H, m), 4.18–4.28 (3H, m)

Compound I-9: Z=single bond, m=n=0, $R^7+R^8=-(CH_2)_2-$, $R^9=R^{10}=H$, 0.87–1.07 (4H, m), 1.22 (3H, d), 1.30 (3H, d), 1.59–1.66 (1H, m), 2.70–2.79 (1H, m), 3.04–3.08 (1H, m), 3.12–3.17 (1H, m), 3.36–3.45 (2H, m), 3.47–3.87 (9H, m), 4.10–4.15 (1H, m), Compound I-10: Z=single bond, m=0, n=1, $R^7=R^8=H$, $R^9=R^{10}=H$, 1.21 (3H, d), 1.30 (3H, d), 1.6–1.7 (1H, m), 2.7–2.8 (1H, m), 2.8–2.9 (2H, m), 3.09 (1H, d), 3.19 (1H, dd), 3.2–3.3 (2H, m), 3.3–3.4 (2H, m), 3.5–3.7 (8H, m), 3.8–3.9 (1H, m), 4.1–4.3 (3H, m)

Compound I-11: Z=single bond, m=n=0, $R^7=H$ $R^8CH_2OH$, $R^9=R^{10}=H$, 2R, 1.22 (3H, d), 1.30 (3H, d), 1.75–1.84 (1H, m), 2.83–2.94 (1H, m), 3.25 (1H, dt), 3.36–3.44 (2H, m), 3.46 (1H, dd), 3.63–3.80 (8H, m), 3.80–3.95 (3H, m), 4.21–4.29 (2H, m), 4.40–4.47 (2H, m), Compound I-12: Z=single bond, m=n=0, $R^7=H$ $R^8=CH_2OH$, $R^9=R^{10}=H$, 2S, 1.22 (3H, d), 1.30 (3H, d), 1.75–1.84 (1H, m), 2.83–2.93 (1H, m), 3.25 (1H, m), 3.36–3.44 (2H, m), 3.45 (1H, dd), 3.63–3.78 (8H, m), 3.78–3.95 (3H, m), 4.21–4.29 (2H, m), 4.40–4.47 (2H, m), Compound I-13: Z=single bond, $R^5=H$, $R^6=OH$ m=1, n=0, $R^7=R^8=R^9=R^{10}=H$, 2S, 1.23 (3H, d), 1.32 (3H, d), 1.6–1.7 (1H, m), 2.65–2.85 (1H, m), 3.05–4.90 (15H, m), 4.15–4.30 (3H, m), 4.75–4.85 (1H, m), Compound I-14: Z=single bond, $R^5=H$, $R^6F$, m=1, n=0, $R^7=R^8=R^9=R^{10}=H$, 2R, 1.22 (3H, d), 1.31 (3H, d), 1.72–1.90 (1H, m), 2.81–2.89 (1H, m), 3.19–3.22 (1H, m), 3.32–3.48 (5H, m), 3.60–3.82 (8H, m), 3.85–3.92 (1H, m), 4.21–4.29 (2H, m), 4.32–4.40 (1H, m), 5.63–5.68 (0.5H, m), 5.75–5.80 (0.5H, m)

Compound I-15: Z=single bond, m=0, n=2, $R^7=H$ $R^8CH_2OH$, $R^9=R^{10}=H$, 4S, 1.22 (3H, d), 1.30 (3H, d), 1.58–1.64 (1H, m), 1.77–1.92 (2H, m), 2.56–2.77 (3H, m), 3.02–3.07 (1H, m), 3.07–3.27 (1H, m), 3.37–3.45 (2H, m), 3.45–3.82 (12H, m), 4.03–4.14 (1H, m), 4.20–4.30 (2H, m)

Compound I-16: Z=$CR^{11}R^{12}$, $R^5=R^6=H$, m=2, n=0, $R^7=R^8=R^9=R^{10}=R^{11}=H$, $R^{12}=CH_3$, 1.20 (3H, d), 1.29 (3H, d), 1.31 (3H, d), 1.59–1.66 (1H, m), 1.78–1.88 (1H, m), 1.93–2.02 (1H, m), 2.53–2.68 (2H, m), 2.69–2.79 (1H, m), 3.04–3.09 (1H, m), 3.14–3.19 (1H, m), 3.37–3.47 (3H, m), 3.60–3.71 (8H, m), 3.78–3.82 (1H, m), 4.12–4.28 (3H, m)

Compound I-17: Z=$CR^{11}R^{12}$, $R^5=R^6=H$, m=1, n=0, $R^7=R^8=R^9=R^{10}=R^{11}=H$, $R^{12}OH$, 1.22 (3H, d), 1.31 (3H, d), 1.64–1.74 (1H, m), 2.64–2.71 (1H, m), 2.71–2.85 (2H, m), 3.02 (1H, dd), 3.14 (1H, m), 3.22 (1H, dd), 3.26 (1H, dd), 3.40 (2H, m), 3.45 (1H, dd), 3.57–3.82 (8H, m), 3.86 (1H, m), 4.20–4.36 (4H, m)

Compound I-18: Z=single bond, $R^5=H$, $R^6=OH$, m=1, n=2, $R^7=R^8=R^9=R^{10}=H$, 2S, 1.19 (3H, d), 1.28 (3H, d), 1.3–1.8 (5H, m), 2.65–2.80 (1H, m), 3.00–3.15 (3H, m), 3.15–3.20 (1H, m), 3.35–3.45 (2H, m), 3.50–3.85 (9H, m), 4.10–4.25 (3H, m), 4.65–4.70 (1H, m)

Compound I-19: Z=single bond, m=0, n=3, $R^7=R^8=R^9=R^{10}=H$, 1.21 (3H, d), 1.30 (3H, d), 1.5–1.8 (5H, m), 2.5–2.6 (2H, m), 2.7–2.8 (1H, m), 3.01 (2H, t), 3.0–3.1 (1H, m), 3.16 (1H, dd), 3.5–3.7 (8H, m), 3.8–3.9 (1H, m), 4.1–4.3 (3H, m)

Compound I-20: Z=single bond, m=0, n=4, $R^7=R^8=R^9=R^{10}=H$, 1.20 (3H, d), 1.29 (3H, d), 1.35–1.45 (2H, m), 1.55–1.75 (5H, m), 2.50 (2H, t), 2.65–2.80 (1H, m), 2.99 (2H, t), 3.00–3.10 (1H, m), 3.16 (1H, dd), 3.35–3.45 (2H, m), 3.55–3.75 (8H, m), 3.75–3.85 (1H, m), 4.10–4.30 (3H, m)

(In each of the above compounds I-4, I-5, I-6, I-11, I-12, I-13, I-14, I-15 and I-18, configuration in the partial structure of formula (IVa) is shown together with a numeral which indicates the position number of corresponding atom in the partial structure of (IVa) when the carbonyl carbon is defined as the 1-position.)

[Inventive Example 5]

(1R,5S,6S,8R,2'S,4'S)-2-(2-(4-(2-(2-aminoethyl) acetyl)piperazine-1-yl)carbonylpyrrolidine-4-yl) thio-6-(1-hydroxyethyl)-1-methylcarbapenem-3-carboxylic acid

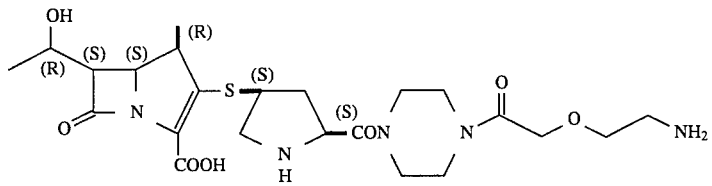

1) To 181 mg of p-nitrobenzyl (1R,5S,6S,8R)-6-(1-hydroxyethyl) -1-methyl-2-oxocarbapenam-3-carboxylate dissolved in acetonitrile and cooled on an ice bath were added dropwise 0.131 ml of diisopropylethylamine and 0.155 ml of diphenylphosphoryl chloride, followed by 3 hours of stirring at the same temperature. After cooling down to −35° C., to this were added 272 mg of (2S,4S)-1-(p-nitrobenzyloxycarbonyl) -2-(4-(2-(2-(p-nitrobenzyloxycarbonyl-amino) ethoxyacetyl)piperazine-1-yl)carbonyl)-4-mercaptopyrrolidine and 0.087 ml of diisopropylethylamine in that order, followed by 16 hours of reaction at the same temperature.

After evaporation of the solvent under a reduced pressure, the residue was subjected to purification by a silica gel column chromatography to yield 546 mg of p-nitrobenzyl (1R,5S,6S,8R,2'S,4'S)-2-(1-(p-nitrobenzyloxycarbonyl) -2-(2-(4-(2-(2-p-nitrobenzyloxycarbonylamino)-ethoxy) acetyl)piperazine-1-yl)carbonylpyrrolidine-4-yl)thio-6-(1-hydroxyethyl) (1-hydroxyethyl)-1-methylcarbapenem-3-carboxylate.

NMR (CDCl₃) δ: 1.10–1.60 (6H, m), 1.70–2.20 (1H, m), 2.50–2.90 (1H, m), 2.90–3.95 (15H, m), 3.95–4.40 (6H, m), 4.55–4.90 (1H, m), 5.19 (4H, s), 5.20 (1H, d), 5.51 (1H, d), 5.92–6.23 (1H, m), 7.50 (4H, d), 7.60 (4H, d), 8.19 (6H, d)

2) A 546 mg portion of p-nitrobenzyl (1R,5S,6S,8R,2'S,4'S)-2-(1-(p-nitrobenzyloxycarbonyl)-2-(2-(4-(2 -(2-p-nitrobenzyloxycarbonylamino)ethoxy)acetyl)-piperazine -1-yl)carbonylpyrrolidine-4-yl)thio-6-(1-hydroxyethyl) -1-methylcarbapenem-3-carboxylate was dissolved in a mixture of 30 ml of tetrahydrofuran and 40 ml of phosphate buffer, and the solution was subjected to 3 hours of catalytic reduction in the presence of 180 mg of platinum oxide under 4 atmospheric pressure.

After removing the catalyst by filtration and concentrating the filtrate, the thus obtained residue was subjected to a column chromatography using Diaion HP-20, and the eluate was further purified by HPLC to yield 21 mg of the title compound.

NMR (D₂O) δ: 1.21 (3H, d), 1.29 (3H, d), 1.62–1.69 (1H, m), 2.71–2.81 (1H, m), 3.08–3.12 (3H, m), 3.19–3.26 (3H, m), 2.38–3.44 (2H, m), 3.50–3.55 (2H, m), 3.63–3.73 (6H, m), 3.80–3.83 (3H, m), 4.18–4.28 (3H, m), 4.29 (2H, d)

[Inventive Example 6]

(1R,5S,6S,8R,2'S,4'S) -2-(2-(4-(2-( (2S)-2-carboxy-2-aminoethylthio acetyl)piperazine-1-yl)carbonylpyrrolidine-4-yl) thio-6-(1-hydroxyethyl)-1-methyl carbapenem-3-carboxylic acid

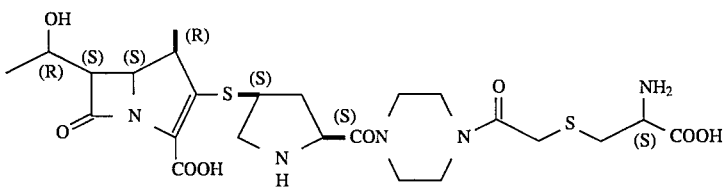

1) To 272 mg of p-nitrobenzyl (1R,5S,6S,8R)-6-(1-hydroxyethyl) -1-methyl-2-oxocarbapenam-3-carboxylate dissolved in acetonitrile and cooled at 0° C. were added 0.222 ml of diphenylphosphoryl chloride and 0.194 ml of diisopropylethylamine, followed by 2 hours of reaction at the same temperature.

After cooling down to −30° C., to this were added 680 mg of (2S,4S)-1-(p-nitrobenzyloxycarbonyl)-2-(4-(2-((2S)-2-(p-nitrogenzyloxycarbonyl) -2-(p-nitrobenzyloxycarbonylamino)ethylthio) acetyl)piperazine-1-yl)carbonyl)-4-mercaptopyrrolidine and 0.196 ml of diisopropylethylamine, followed by 2.5 hours of reaction at the same temperature. Thereafter, the resulting reaction solution was subjected to purification by a silica gel column chromatography to yield 630 mg of p-nitrobenzyl (1R,5S,6S,8R,2'S,4'S)-2-(1-p-nitrobenzyloxycarbonyl) -2-(4-(2-((2S)-2-(p-nitrobenzyloxycarbonyl)-2-(p-nitrobenzyloxycarbonylamino)ethylthio) acetyl)-piperazine -1-yl)carbonyl)pyrrolidine-4-yl)thio-6-(1-hydroxyethyl) -1-methylcarbapenem-3-carboxylate.

(CDCl₃) δ: 1.1–1.4 (6H, m), 1.6–2.1 (1H, m), 2.4–2.9 (1H, m), 2.9–4.4 (19H, m), 4.5–4.9 (2H, m), 5.22 (4H, s), 5.29 (2H, s), 5.1–5.3 (1H, m), 5.51 (1H, d), 7.4–7.7 (8H, m), 8.1–8.3 (8H, m)

2) A 630 mg portion of p-nitrobenzyl (1R,5S,6S,8R,2'S,4'S)-2-(1-p-nitrobenzyloxycarbonyl-2-(4-(2-((2S )-2-(p-nitrobenzyloxycarbonyl)-2-(p-nitrobenzyloxycarbonylamino) ethylthio)acetyl)piperazine-1-ylcarbonyl)-pyrrolidine -4-yl)thio-6-(1-hydroxyethyl)-1-methylcarbapenem-3 -carboxylate was dissolved in a mixture solution consisting of tetrahydrofuran and phosphate buffer, and the resulting solution was subjected to 2 hours of catalytic reduction in the presence of 270 mg of platinum oxide in a stream of hydrogen of 4.5 atmospheric pressure. After removing the catalyst by filtration and concentrating the filtrate, the thus obtained residue was subjected to a column chromatography using Diaion HP-20, and a fraction containing the compound of interest was further purified by HPLC to yield 118.5 mg of the title compound.

[Inventive Example 9]
(1R,5S,6S,8R,2'S,4'S)-2-(2-( 4-(2-(2-aminoacetyl) aminoacetyl)piperazine-1-yl)carbonylpyrrolidine-4-yl) thio-6-(1-hydroxyethyl)-1-methylcarbapenem-3-carboxylic acid

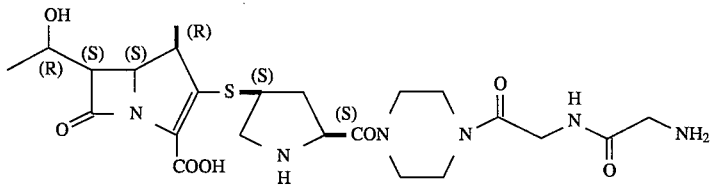

NMR (D₂O) δ: 1.20 (3H, d), 1.28 (3H, d), 1.75–1.85 (1H, m), 2.80– 2.95 (1H, m) 3.05–3.15 (1H, m), 3.15–3.20 (1H, m), 3.20–3.30 (1H, m), 3.35–3.50 (3H, m), 3.60– 3.75 (10H, m), 3.90–3.95 (2H, m), 4.20–4.30 (2H, m), 4.40–4.50 (1H, m)

NMR (D₂O) δ: 1.23 (3H, d), 1.31 (3H, d), 1.57–1.65 (1H, m), 2.69– 2.78 (1H, m), 3.02–3.08 (1H, m), 3.11–3.16 (1H, m), 3.38–3.45 (1H, m), 3.43 (2H, s), 3.54–3.91 (9H, m), 4.08–4.14 (1H, m), 4.16–4.30 (4H, m)

The following compounds were obtained in the same manner.

[Reference Example 5]

[Inventive Example 7]
(1R, 5S, 6S, 8R, 2' S, 4'S )-2-(2-(4-(2-((2R)-2-carboxy-2-aminoethylthio) acetyl)piperazine-1-yl)carbonylpyrrolidine-4-yl)thio -6-(1-hydroxyethyl )-1-methylcarbapenem-3-carboxylic acid

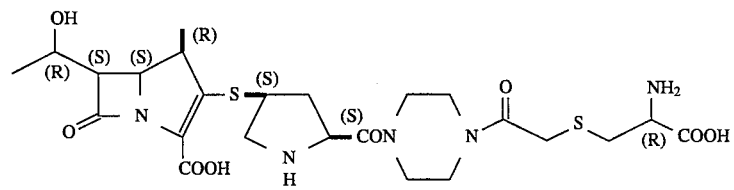

NMR (D₂O) δ: 1.20 (3H, d), 1.28 (3H, d), 1.75–1.85 (1H, m), 2.85– 2.95 (1H, m), 3.05–3.15 (1H, m), 3.15–3.20 (1H, m), 3.20–3.30 (1H, m), 3.35–3.50 (3H, m), 3.60– 3.75 (10H, m), 3.90–3.95 (2H, m), 4.20–4.30 (2H, m), 4.47 (1H, t)

[Inventive Example 8]
(1R,5S,6S,8R,2'S,4'S)-2-(2-( 4-(2-(2-aminoethylthio) acetyl)piperazine-1-yl)carbonylpyrrolidine-4-yl) thio-6-(1-hydroxyethyl )-1-methylcarbapenem-3-carboxylic acid

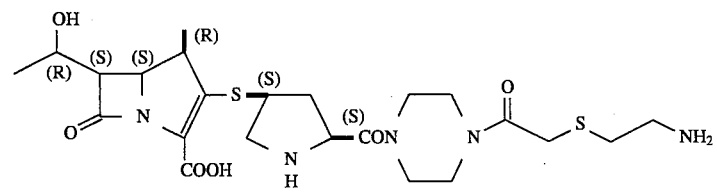

NMR (D₂O) δ: 1.22 (3H, d), 1.30 (3H, d), 1.64–1.70 (1H, m), 2.74– 2.8.5 (1H, m), 2.92–2.95 (2H, m), 3.13 (1H, d), 3.17–3.26 (3H, m), 3.39–3.45 (2H, m), 3.58–3.72 (10H, m), 3.84–3.86 (1H, m), 4.21–4.31 (3H, m), 4.76–4.85 (1H, m)

(2S, 4S )-1-(p-nitrobenzyloxycarbonyl)-2-(4-(2-(2-(p-nitrobenzyloxycarbonylamino) ethoxy)acetyl)piperazine-1-yl) carbonyl-4-mercaptopyrrolidine

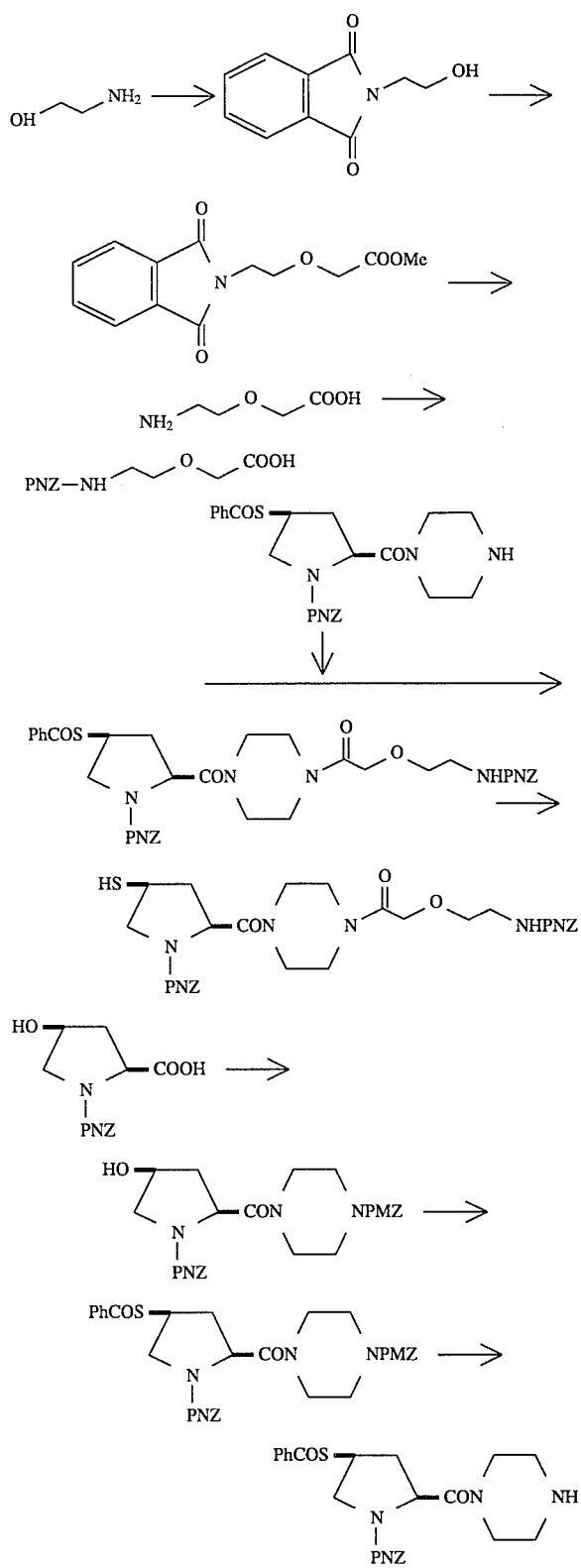

1) A 6.11 g portion of ethanolamine and 14.81 g of phthalic anhydride were stirred in 100 ml of toluene for 3 hours with heating. After concentration of the reaction solution, a residue was crystallized from chloroform, collected by filtration and then dried to yield 17.2 g of white 2-phthalimidoethanol.
NMR (CDCl$_3$) δ: 3.84 (4H, s), 7.6–8.0 (4H, m)

2) A 3.00 g portion of sodium hydride was added gradually to 9.65 g of 2-phthalimidoethanol which has been dissolved in 200 ml of tetrahydrofuran, and the mixture was refluxed for 2 hours, followed by dropwise addition of 7.65 g of methyl bromoacetate to the reaction mixture and subsequent overnight stirring at room temperature. After removing insoluble material by filtration, the resulting filtrate was concentrated and extracted with chloroform, and an organic layer was washed with water and dried over sodium sulfate, followed by evaporation of the solvent under a reduced pressure and. subsequent purification of the resulting residue by a silica gel column chromatography, thereby obtaining 4.81 g of methyl 2-(2-phthalimidoethoxy) acetate in a yellow oily form.
NMR (CDCl$_3$) δ: 3.63 (3H, s), 3.7–4.0 (4H, m), 4.10 (2H, s), 7.6– 8.0 (4H, m)

3) Methyl 2-(2-phthalimidoethoxy) acetate was suspended in 50 ml of 6N hydrochloric acid and subjected to 17 hours of reflux with heating. Crystals thus precipitated were filtered off and washed with 1N hydrochloric acid, and the filtrate was concentrated. The thus obtained residue was dissolved in 1N hydrochloric acid, subjected to cationic ion exchange resin IR-120, washed with water and then eluted with 2N aqueous ammonia, followed by concentration of the eluted fraction under a reduced pressure to yield 873 mg of 2-(2-aminoethoxy)acetic acid.
NMR (D$_2$O) δ: 3.20 (2H, t), 3.76 (2H, t), 3.97 (2H, s)

4) With cooling on an ice bath, to 596 mg of 2-(2-aminoethoxy)acetic acid dissolved in 10 ml of water was added an ether solution of 883 mg sodium bicarbonate and 1.29 g p-nitrobenzyloxycarbonyl chloride in dropwise manner. After stirring the reaction solution for 17 hours at room temperature, the resulting aqueous layer was collected, adjusted to acidic with concentrated hydrochloric acid and extracted with ethyl acetate, and the resulting organic layer was washed with water and dried over sodium sulfate, followed by evaporation of the solvent under a reduced pressure to yield 1.48 g of 2-(2-(p-nitrobenzyloxycarbonylamino)ethoxy)acetic acid.
NMR (CDCl$_3$) δ: 3.26–3.80 (4H, m), 4.12 (2H, s), 5.20 (2H, s), 5.65– 5.93 (1H, m), 7.50 (2H, d), 8.18 (2H, d)

5) To 100 ml of tetrahydrofuran were added 14.9 g of (2S,4R)-1-(p-nitrobenzyloxycarbonyl)-4-hydroxyproline, 12.4 g of dicyclohexylcarbodiimide and 6.75 g of N-hydroxybenzotriazole, followed by 1 hour of reaction at room temperature to yield (2S,4R)-1-(p-nitrobenzyloxycarbonyl)-4-hydroxyproline N-hydroxybenzotriazole ester. To the solution was added 16.5 g of 1-(p-methoxybenzyloxycarbonyl)piperazine, followed by 2 hours of reaction with stirring at room temperature. After completion of the reaction, dicyclohexylurea was removed by filtration, and the filtrate was evaporated under a reduced pressure. A residue was dissolved in chloroform and subjected to washing with 10% citric acid and water, and dried over sodium sulfate, followed by evaporation of the solvent under a reduced pressure to yield oily residue. This was applied to a silica gel column chromatography and eluted with chloroform and a mixture of chloroform and methanol to yield 16.5 g of (2S,4R)-1-(p-nitrobenzyloxycarbonyl)-2-(4-(p-methoxybenzyloxycarbonyl) piperazine-1-yl)carbonyl-4-hydroxypyrrolidine as the compound of interest.

NMR (CDCl$_3$) δ: 0.90–1.40 (2H, m), 3.00–3.90 (11H, m), 3.80 (3H, s), 4.40–4.70 (1H, m), 4.90–5.44 (4H, m), 6.75–7.02 (2H, m), 7.20–7.60 (4H, m), 8.08–8.30 (2H, m)

6) A 11.8 g portion of triphenylphosphine was dissolved in 200 ml of tetrahydrofuran, and, with cooling at −20° C., 7.06 ml of diethyl azodicarboxylate was added dropwise to the solution.

To this, 40 minutes thereafter, was gradually added dropwise a tetrahydrofuran solution (200 ml) containing 15.9 g of (2S,4R)-1-(p-nitrobenzyloxycarbonyl)-2-(4-(p -methoxybenzyloxycarbonyl)piperazine-1-yl)carbonyl-4-hydroxypyrrolidine and 5.2 ml of thiobenzoic acid. After overnight reaction with stirring at room temperature, tetrahydrofuran was removed by evaporation under a reduced pressure, a residue was dissolved in 500 ml of ethyl acetate and washed with sodium bicarbonate aqueous solution, and the resulting organic layer was washed with water and dried over sodium sulfate, followed by evaporation of the solvent under a reduced pressure. The thus obtained (2S,4S)-1-(p-nitrobenzyloxycarbonyl) -2-(4-(p-methoxybenzyloxycarbonyl) piperazine-1-yl)carbonyl-4-benzoylthiopyrrolidine was used in the following reaction without purification.

7) The crude compound obtained above was added to an ice-cold mixture solution consisting of 200 ml of trifluoroacetic acid and 50 ml of anisole, followed by 1 hour of reaction at room temperature. After evaporation of trifluoroacetic acid under a reduced pressure, a residue was dissolved in ethyl acetate and neutralized with sodium bicarbonate aqueous solution, and the resulting ethyl acetate layer was collected, washed with water and dried over sodium sulfate, followed by evaporation of the solvent under a reduced pressure. The thus obtained residue was subjected to a silica gel column chromatography to collect chloroform-methanol mixture-eluted fractions from which 12 g of (2S,4S)-1-(p-nitrobenzyloxycarbonyl) -2-(piperazine-1-yl)carbonyl-4-benzoylthiopyrrolidine was obtained.

NMR (CDCl$_3$) δ: 1.8–2.3 (1H, m), 2.6–3.3 (5H, m), 3.3–4.0 (5H, m), 4.0–4.4 (2H, m), 4.6–5.0 (1H, m), 5.23 (2H, s), 7.3–7.7 (5H, m), 17.8–8.0 (2H, m), 8.23 (2H, d)

8) In 10 ml of tetrahydrofuran was dissolved 209 mg of 2-(2-(p-nitrobenzyloxycarbonylamino)ethoxy)acetic acid, followed by stirring on an ice bath. To this were added 161 mg of 1-hydroxybenzotriazole and 433 mg of dicyclohexylcarbodiimide, followed, after 1 hour of stirring at the same temperature, by the addition of 523 mg of (2S,4S)-1-(p-nitrobenzyloxycarbonyl)-2-(piperazine-1-yl)carbonyl-4 -benzoylthiopyrrolidine and 0.146 m of triethylamine and subsequent 1 hour of stirring. After removing insoluble material by filtration, the resulting filtrate was evaporated under a reduced pressure, and a residue was subjected to a silica gel column chromatography to yield 402 mg of (2S,4S)-1-(p-nitrobenzyloxycarbonyl)-2-(4-(2-(2) -(p-nitrobenzyloxycarbonylamino) ethoxy)acetyl)piperazine-1-yl)carbonyl-4-benzoylthiopyrrolidine as the compound of interest.

NMR (CDCl$_3$) δ: 1.80–2.30 (1H, m), 2.60–3.00 (1H, m), 3.20–4.00 (13H, m), 4.00–4.40 (4H, m), 4.60–5.00 (1H, m), 5.00–5.35 (5H, m), 7.35–7.65 (7H, m), 7.83–8.00 (2H, m), 8.00–8.33 (4H, m)

9) To 402 mg of (2S,4S)-1-(p-nitrobenzyloxycarbonyl)-2(4-(2-(2 (2-(2-(p-nitrobenzyloxycarbonylamino)ethoxy) acetyl) -piperazine-1-yl)carbonyl-4-benzoylthiopyrrolidine dissolved in 5 ml of tetrahydrofuran was added 5 ml of methanol, followed by stirring on an ice bath. A 69 mg portion of sodium methoxide was added to the above solution and stirred for 30 minutes. After neutralization of the reaction solution with concentrated hydrochloric acid and subsequent evaporation of the solvent under a reduced pressure, the resulting residue was subjected to a silica gel column chromatography to yield 272 mg of the title compound.

NMR (CDCl$_3$) δ: 1.70–2.16 (1H, m), 2.50–2.95 (1H, m), 2.95–3.93 (13H, m), 3.93–4.30 (4H, m), 4.50–4.85 (1H, m), 5.00–5.32 (5H, m), 7.51 (4H, d), 8.20 (4H, d)

[Reference Example 6]
(2S,4S)-1-(p-nitrobenzyloxycarbonyl)-2-(4-(2-((2S)-2-(p-nitrobenzyloxycarbonyl) -2-(p-nitrobenzyloxycarbonylamino) ethylthio)acetyl)piperazine-1-yl)carbonyl-4-mercaptopyrrolidine

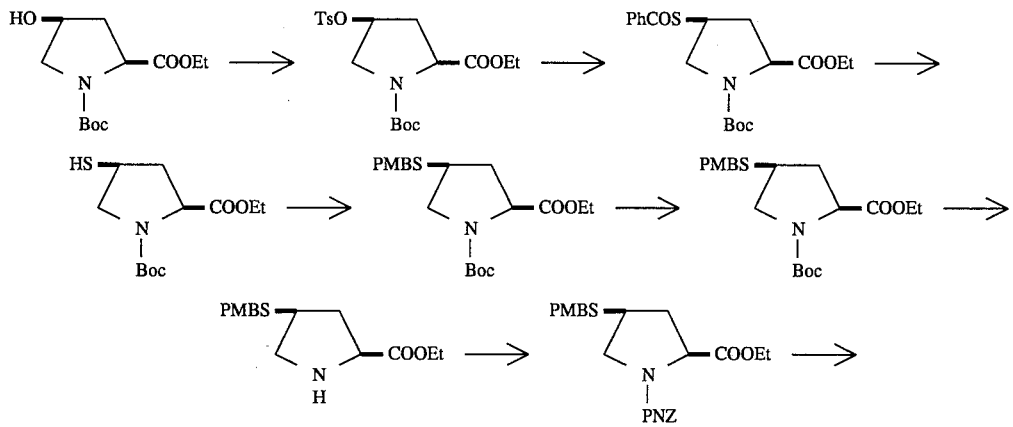

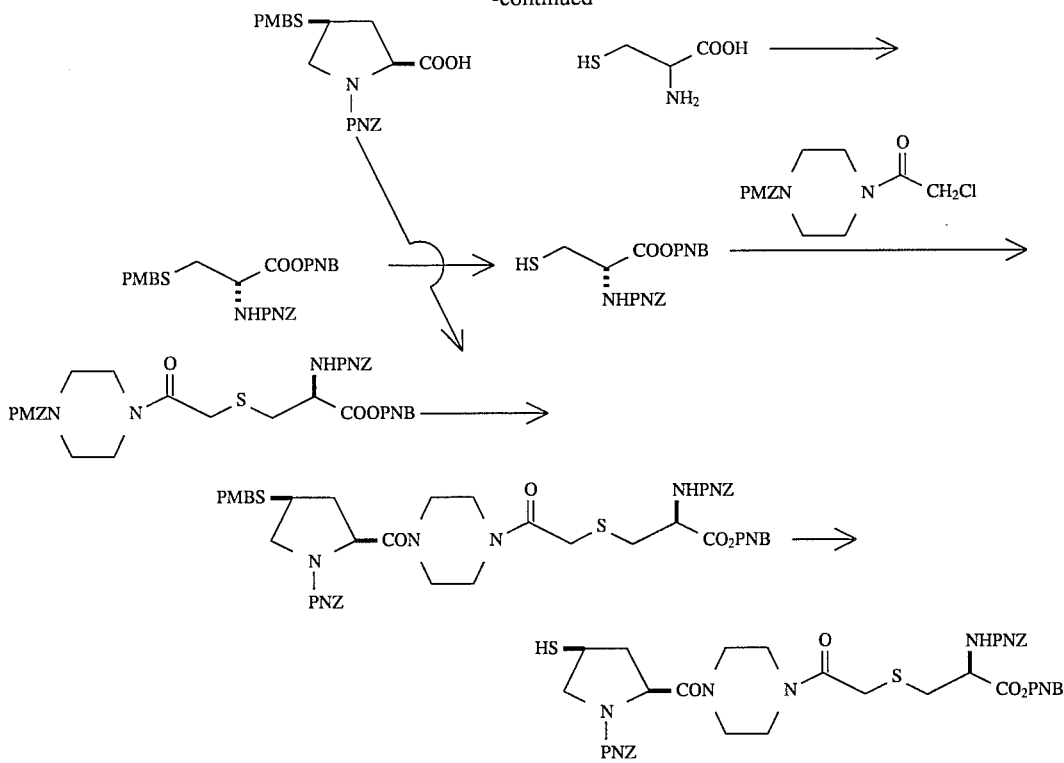

-continued

1) To 5.05 g of D-cysteine hydrochloride dissolved in 4 N sodium hydroxide and cooled on an ice bath was added dropwise 9.39 ml of p-methoxybenzyl chloride, followed by 2 hours of stirring at room temperature. The resulting reaction solution was washed with ether and acidified with concentrated hydrochloric acid, and a crystal was collected by filtration to yield 7.78 g of S-p-methoxybenzyl-D-cysteine in the form of pale yellow crystals.

A 7.025 g portion of the thus obtained S-p-methoxybenzyl compound was dissolved in an aqueous-acetonitrile, and, with cooling on an ice bath, to this were added 12.75 g of sodium bicarbonate and 7.09 g of p-nitrobenzyloxycarbonyl chloride, and the mixture was stirred for 1.5 hours at room temperature. The reaction solution was washed with ether, acidified with concentrated sulfuric acid and extracted with ethyl acetate, the resulting organic layer was washed with water and dried over sodium sulfate and then the solvent was removed by evaporation under a reduced pressure, thereby yielding 6.47 g of S-p-methoxybenzyl-N-p-nitrobenzyloxy-carbonylcysteine as an oil.

A 2.31 ml portion of triethylamine was added to an ice-cold dimethylformamide solution containing 5.81 g of the thus obtained p-nitrobenzyloxycarbonyl compound and 3.28 g of p-nitrobenzyl bromide, and the mixture was stirred for 1 hour at the same temperature and then for 3 hours at room temperature. After removing the solvent by evaporation under a reduced pressure, the thus obtained residue was dissolved in ethyl acetate, washed with water and dried over sodium sulfate, followed by evaporation of the solvent under a reduced pressure and subsequent purification of the resulting residue by a silica gel column chromatography to yield 7.31 g of S-p-methoxybenzyl-N-p-nitrobenzyloxycarbonyl-D-cysteine-p-nitrobenzyl ester.

NMR (CDCl$_3$) δ: 2.89 (2H, d), 3.66 (2H, s), 3.77 (3H, s), 4.5–4.6 (1H, m), 5.21 (2H, s), 5.26 (2H, s), 5.5–5.7 (1H, m), 6.80 (2H, d), 7.16 (2H, d), 7.4–7.6 (4H, m), 8.18 (4H, d)

2) A 766 mg portion of S-p-methoxybenzyl-N-p-nitrobenzyloxycarbonyl -D-cysteine-p-nitrobenzyl ester was dissolved in a mixture of trifluoroacetic acid and anisole and cooled on an ice bath, to which was subsequently added 0.183 ml of trifluoromethanesulfonic acid, and the resulting mixture was stirred for 5 hours at room temperature. After evaporation of the solvent under a reduced pressure, the resulting residue was mixed with ethyl acetate, washed with sodium bicarbonate aqueous solution and saturated sodium chloride aqueous solution in that order and then dried over sodium sulfate, followed by evaporation of the solvent under a reduced pressure to yield 920 mg of N-p-nitrobenzyloxy-carbonyl-D-cystein-p-nitrobenzyl ester.

A 0.1.86 ml portion of triethylamine was added to a dichloromethane solution containing 319 mg of the thus obtained compound and 217 mg of 1-p-methoxybenzyloxycarbonyl -4-(2-chloroacetyl)piperazine, and the mixture was subjected to 2 hours of reflux with heating. After evaporation of the solvent under a reduced pressure, the residue was purified by a silica gel column chromatography to yield 453 mg of 1-p-methoxybenzyloxycarbonyl-4-(2 -((2S)-(p-nitrobenzyloxycarbonyl) -2-(p-nitrobenzyloxycarbonylamino)ethylthio)acetyl)piperazine as a pale yellow oil.

NMR (CDCl$_3$) δ: 3.11 (2H, d), 3.3–3.7 (10H, m), 3.80 (3H, s), 4.5– 4.9 (1H, m), 5.08 (2H, s), 5.22 (2H, s), 5.28 (2H, s), 5.5–5.7 (1H, m), 6.89 (2H, d), 7.29 (2H, d), 7.52 (4H, d), 8.17 (2H, d), 8.19 (2H, d)

3) To 193 g of (2S,4R)-1-(t-butoxycarbonyl)-2-ethoxycarbonyl -4-hydroxypyrrolidine dissolved in 500 ml of pyridine and cooled on an ice bath was added 213 g of p-toluenesulfonyl chloride, followed by 20 hours of stirring at room temperature. The reaction mixture was concentrated, and the resulting residue was dissolved in ethyl acetate, washed with water, 10% citric acid aqueous solution, 5% sodium bicarbonate aqueous solution and water in that order, followed by evaporation of the solvent under a reduced pressure to yield 289 g of (2S,4R)-1-(t-butoxycarbonyl)-2-ethoxycarbonyl-4 -(p-toluenesulfonyloxy)pyrrolidine.

Next, 36.4 g of thiobenzoic acid was dissolved in 300 ml of dimethylformamide and cooled on an ice bath, to which was subsequently added 10.5 g of sodium hydride. To this were added 102 g of (2S,4R)-1-(t-butoxycarbonyl)-2-ethoxycarbonyl -4-(p-toluenesulfonyloxy)pyrrolidine dissolved in 200 ml of dimethylformamide and 37.5 g of sodium iodide, followed by heating at 80° C. for 3 hours. After concentration of the reaction mixture, the thus obtained residue was dissolved in .benzene, and the resulting organic layer was washed with 5% sodium bicarbonate aqueous solution, 10% citric acid aqueous solution and water in that order, followed by drying over sodium sulfate and subsequent evaporation of the solvent under a reduced pressure. The resulting residue was purified by a silica gel column chromatography to yield 66 g of (2S,4S)-1-(t-butoxycarbonyl)-2-ethoxycarbonyl -4-benzoylthiopyrrolidine.

With cooling on an ice bath, 66 g of the thus obtained compound was added to sodium ethoxide which has been prepared from 300 ml of ethanol and 4.4 g of sodium, and the resulting mixture was subjected to 30 minutes of reaction at the same temperature. With cooling on an ice bath, 27.4 g of p-methoxybenzyl chloride was added to the reaction solution, and the resulting mixture was stirred for 2 hours at the same temperature and then for 15 hours at room temperature. After concentration. of the reaction mixture, the thus obtained residue was mixed with ethyl acetate, and the resulting organic layer was washed with water and dried over sodium sulfate, followed by evaporation of the solvent under a reduced pressure and subsequent purification of the resulting residue by a silica gel column chromatography to yield 56 g of (2S,4S)-1-(t-butoxycarbonyl)-2-ethoxycarbonyl-4-(p-methoxybenzyl)thiopyrrolidine.

A 3.95 g portion of the thus obtained compound was dissolved in 20 ml of trifluoroacetic acid and subjected to 1 hour of reaction at room temperature, the solvent was removed by evaporation under a reduced pressure, the thus obtained residue was neutralized with sodium bicarbonate aqueous solution and extracted with ethyl acetate and the resulting organic layer was washed with water and dried over sodium sulfate, followed by evaporation of the solvent under a reduced pressure to yield 2.8 g of (2S,4S)-2-ethoxycarbonyl-4-(p-methoxybenzyl) thiopyrrolidine.

The thus obtained compound was dissolved in 20 ml of tetrahydrofuran, and, with cooling on an ice bath, 1.4 ml of triethylamine and 2.2 g of p-nitrobenzyloxycarbonyl chloride were added to the resulting solution, and allowed to 3 hours of reaction. After removing the solvent by evaporation under a reduced pressure, the thus obtained residue was mixed with ethyl acetate, and the resulting organic layer was washed with water and dried over sodium sulfate, followed by evaporation of the solvent under a reduced pressure to yield 4.5 g of (2S,4S)-1-p-nitrobenzyloxycarbonyl-2-ethoxycarbonyl -4-(p-methoxybenzyl)thiopyrrolidine. This was dissolved in 50 ml of ethanol, mixed with 24 ml of 1N sodium hydroxide and stirred for 1.5 hours, followed by evaporation of the solvent under a reduced pressure and subsequent dilution of the resulting concentrated solution with water and washing with ethyl acetate. The aqueous layer thus collected was acidified with citric acid aqueous solution and extracted with ethyl acetate and the resulting organic layer was washed with water and dried over sodium sulfate, followed by evaporation of the solvent under a reduced pressure to yield 2.9 g of (2S,4S)-1-(p-nitrobenzyloxycarbonyl)-4-(p-methoxybenzyl)thioproline.

NMR (CDCl$_3$) δ: 1.8–2.8 (2H, m), 2.9–3.6 (3H, m), 3.73 (2H, s), 3.80 (3H, s), 4.34 (1H, t), 5.24 (2H, s), 6.21 (1H, s), 6.86 (2H, d), 7.23 (2H, d), 7.4–7.6 (2H, m), 8.1–8.3 (2H, m)

4) To 278 mg of (2S,4S)-1-(p-nitrobenzyloxycarbonyl)-4-(p-methoxybenzylthio)proline dissolved in 5 ml of dichloromethane were added 0.109 ml of oxalyl chloride and one drop of dimethylformamide, followed by 1.5 hours of reaction and subsequent evaporation of the solvent under a reduced pressure to yield (2S,4S)-1-(p-nitrobenzyloxycarbonyl)-4 -(p-methoxybenzyl)thioproline chloride.

A 453 mg portion of 1-(p-methoxybenzyloxycarbonyl)-4-(2-((2S) -2-(p-nitrobenzyloxycarbonyl)-2-(p-nitrobenzyloxycarbonylamino)ethylthio)acetyl)piperazine obtained in the foregoing step 2) was allowed to react with 3 ml of trifluoroacetic acid for 30 minutes, and then the solvent was removed by evaporation under a reduced pressure. The resulting residue was dissolved in dichloromethane, mixed with 2.18 ml of triethylamine and then allowed to react with the just obtained acid chloride at an elevated temperature, and the resulting product was subjected to purification by a silica gel column chromatography to yield 494 mg of (2S,4S)-1-(p-nitrobenzyloxycarbonyl) -2-(4-(2-((2S)-2-(p-nitrobenzyloxycarbonyl)-2 -(p-nitrobenzyloxycarbonylamino) ethylthio)acetyl)piperazine-1-ylcarbonyl)-4-(p-methoxybenzyl) thiopyrrolidine.

NMR (CDCl$_3$) δ: 1.6–2.1 (1H, m), 2.3–2.7 (1H, m), 2.8–3.8 (15H, m), 3.73 (2H, s), 3.78 (3H, s), 4.4–4.8 (2H, m), 5.18 (2H, s), 5.23 (2H, s), 5.29 (2H, s), 6.85 (2H, d), :7.23 (2H, d), 7.4–7.6 (6H, m), 8.1–8.3 (6H, m)

5) To 774 mg of (2S,4S)-1-(p-nitrobenzyloxycarbonyl)-2 -(4-(2-((2S)-2-(p-nitrobenzyloxycarbonyl)-2-(p-nitrobenzyloxycarbonylamino) ethylthio)acetyl)piperazine-1-ylcarbonyl)-4-(pmethoxybenzyl)thiopyrrolidine obtained in the step 4) above and dissolved in a mixture of trifluoroacetic acid and anisole was added 0.021 ml of trifluoromethanesulfonic acid at room temperature, and the resulting mixture was subjected to 4 hours of reaction.

After evaporation of the solvent under a reduced pressure, the resulting residue was purified by a silica gel column chromatography to yield the title compound.

NMR (CDCl$_3$) δ: 1.6–2.1 (2H, m), 2.5–2.8 (1H, m), 2.8–4.2 (15H, m) , 4.4–4.8 (2H, m), 5.23 (4H, s), 5.29 (2H, s), 7.4–7.6 (6H, m), 8.1–8.3 (6H, m)

[Reference Example 7]

(2S,4S)-1-(p-nitrobenzyloxycarbonyl)-2-(4-(2-((2S)-2-(p-nitrobenzyloxycarbonyl) -2-(p-nitrobenzyloxycarbonylamino)ethylthio) acetyl)piperazine-1-yl)carbonyl-4-mercaptopyrrolidine NMR (CDCl$_3$) δ: 1.6–2.2 (2H, m), 2.5–2.9 (1H, m), 2.9–4.2 (15H, m), 4.5–4.8 (2H, m), 5.23 (4H, s), 5.29 (2H, s), 7.4–7.6 (6H, m), 8.1–8.3 (6H, m)

Reference Example 8]

(2S, 4S )-1-(p-nitrobenzyloxycarbonyl) -2-(4-(2-(2-(p-nitrobenzyloxycarbonyl) aminoethylthio)acetyl)piperazine-1-yl carbonyl-4-mercaptopyrrolidine NMR (CDCl$_3$) δ: 1.81–1.92 (1H, m), 2.45–2.82 (4H, m), 3.13–3.64 (14H, m) , 4.00–4.20 (1H, m), 4.59–4.78 (1H, m), 5.19 (4H, s), 5.31–5.59 ((1H, m), 7.51 (4H, d), 8.21 ( 4H, d)

Reference Example 9]

(2S, 4S )-1-(p-nitrobenzyloxycarbonyl )-2-(4-(2-(2-p-nitrobenzyloxycarbonylaminoacetyl) aminoacetyl)piperazine-1-yl) carbonyl -4-mercaptopyrrolidine NMR (CDCl$_3$) δ: 1.70–2.13 (1H, m), 2.50–2.95 (1H, m), 3.10–4.30 (15H, m), 4.50–4.90 (1H, m), 5.00–5.40 (4H, m), 5.64–5.93 (1H, m), 6.92–7.25 (1H, s), 7.50 (4H, d), 8.20 (4H, d)

INDUSTRIAL APPLICABILITY

The present invention can provide an antibiotic which is effective upon various bacterial strains including *Pseudomonas aeruginosa*, excellent in terms of safety and stable against hydrolases such as DHP and the like.

I claim:

1. A compound which is a derivative of carbapenem represented by formula (I):

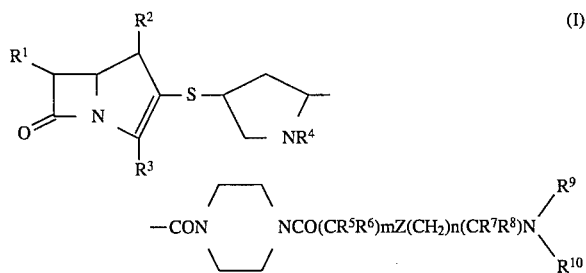

wherein $R^1$ represents a lower alkyl group, a hydroxy lower alkyl group or a hydroxy lower alkyl group which has a protecting group; $R^2$ represents a hydrogen atom or a lower alkyl group; $R^3$ represents a carboxyl group or an esterified carboxyl group; $R^4$ represents an amino protecting group, a hydrogen atom or a lower alkyl group; $R^5$ and $R^6$, which are the same or different, each represents a hydrogen atom, a hydroxyl group, a lower alkyl group, a hydroxy lower alkyl group or a halogen atom, or $R^5$ and $R^6$ together form an alkylene group having 2 to 6 carbon atoms; $R^7$ represents a hydrogen atom, a lower alkyl group, a carboxyl group, a carboxyl group having a protecting group, or a group represented by —$CONR^{71}R^{72}$ where $R^{71}$ and $R^{72}$, which are the same or different, each represents a hydrogen atom or a lower alkyl group; $R^8$ represents a hydrogen atom, a lower alkyl group or a hydroxy lower alkyl group, or $R^7$ and $R^8$ together form an alkylene group having 2 to 6 carbon atoms; $R^9$ and $R^{10}$, which are the same or different, each represents an amino protecting group, a hydrogen atom or a lower alkyl group; Z represents a single bond, an oxygen atom, a sulfur atom, or a group represented by —$CR^{11}R^{12}$—, —$NR^{13}CO$—, —$CONR^{14}$— or —$NR^{15}$— where $R^{11}$ and $R^{12}$, which are the same or different, each represents a hydrogen atom, a hydroxyl group, a lower alkyl group, a hydroxy lower alkyl group or a halogen atom, or $R^{11}$ and $R^{12}$ together form an alkylene group having 2 to 6 carbon atoms, $R^{13}$ and $R^{14}$, which are the same or different, each represents a hydrogen atom or a lower alkyl group and $R^{15}$ represents an amino protecting group, a hydrogen atom or a lower alkyl group; and each of m and n represents an integer of 0 to 6, or a pharmaceutically acceptable salt thereof.

2. The compound or a pharmaceutically acceptable salt thereof according to claim 1, wherein $R^1$ is a 1-hydroxyethyl group.

3. The compound or a pharmaceutically acceptable salt thereof according to claim 1 or 2, wherein said compound is a 6S,8R-6-(1-hydroxyethyl)carbapenem.

4. The compound or a pharmaceutically acceptable salt according to claim 1 or 2, wherein said compound is a 1R,5S,6S,8R-6-(1-hydroxyethyl)-1-methylcarbapenem.

5. The compound according to claim 1 or 2, wherein said compound is (1R,5S,6S,8R,2'S,4'S)-2-((2-((4-((2S)-5-amino-2-hydroxypentanoyl)piperazine-1-yl)carbonyl)pyrrolidine-4-yl)thio)-6-(1-hydroxyethyl)-1-methylcarbapenem-3-carboxylic acid or a pharmaceutically acceptable salt thereof.

6. The compound according to claim 1 or 2, wherein said compound is (1R,5S,6S,8R,2'S,4'S)-2-(2-(4-(2-(2-aminoethoxy)acetyl)piperazine-1-yl)carbonyl-pyrrolidine-4-yl)thio-6-(1-hydroxyethyl)-1-methylcarbapenem-3-carboxylic acid or a pharmaceutically acceptable salt thereof.

* * * * *